United States Patent
Ogino et al.

(10) Patent No.: US 12,251,491 B2
(45) Date of Patent: Mar. 18, 2025

(54) THROMBIN-CARRYING HEMOSTATIC SHEET

(71) Applicants: Astellas Pharma Inc., Chuo-ku (JP); National University Corporation Tokyo Medical and Dental University, Bunkyo-ku (JP)

(72) Inventors: Makoto Ogino, Chuo-ku (JP); Keiichi Yoshihara, Chuo-ku (JP); Yasuharu Kimura, Chuo-ku (JP); Megumi Aoki, Chuo-ku (JP); Toshitaka Yoshii, Bunkyo-ku (JP); Satoru Egawa, Bunkyo-ku (JP)

(73) Assignees: Astellas Pharma Inc., Chuo-ku (JP); National University Corporation Tokyo Medical and Dental University, Bunkyo-ku (JP)

(*) Notice: Subject to any disclaimer, the term of this patent is extended or adjusted under 35 U.S.C. 154(b) by 664 days.

(21) Appl. No.: 17/440,565

(22) PCT Filed: Mar. 19, 2020

(86) PCT No.: PCT/JP2020/012251
§ 371 (c)(1),
(2) Date: Sep. 17, 2021

(87) PCT Pub. No.: WO2020/189755
PCT Pub. Date: Sep. 24, 2020

(65) Prior Publication Data
US 2022/0143263 A1 May 12, 2022

(30) Foreign Application Priority Data
Mar. 20, 2019 (JP) .................................. 2019-052339

(51) Int. Cl.
*A61L 24/04* (2006.01)
*A61K 38/48* (2006.01)
*A61L 24/00* (2006.01)

(52) U.S. Cl.
CPC ........ *A61L 24/043* (2013.01); *A61K 38/4833* (2013.01); *A61L 24/0015* (2013.01); *A61L 24/0036* (2013.01); *C12Y 304/21005* (2013.01); *A61L 2300/254* (2013.01); *A61L 2300/418* (2013.01); *A61L 2400/04* (2013.01)

(58) Field of Classification Search
CPC .............. A61L 24/043; A61L 24/0015; A61L 24/0036; A61L 2300/254; A61L 2300/418; A61L 2400/04; A61K 38/4833; C12Y 304/21005
See application file for complete search history.

(56) References Cited

U.S. PATENT DOCUMENTS

| | | |
|---|---|---|
| 2,558,395 A | 6/1951 | Studer |
| 5,643,596 A | 7/1997 | Pruss et al. |
| 6,649,162 B1 | 11/2003 | Biering et al. |
| 6,977,231 B1 | 12/2005 | Matsuda |
| 2006/0051340 A1 | 3/2006 | Uchida et al. |
| 2006/0088589 A1 | 4/2006 | Gorman et al. |
| 2007/0009578 A1 | 1/2007 | Moller et al. |
| 2008/0095830 A1 | 4/2008 | Van Holten |
| 2011/0021964 A1 | 1/2011 | Larsen et al. |
| 2011/0038847 A1 | 2/2011 | Kawamura et al. |
| 2011/0045034 A1* | 2/2011 | Nur .................... A61L 15/44 424/94.64 |
| 2011/0086175 A1 | 4/2011 | Dey et al. |
| 2011/0251574 A1 | 10/2011 | Hedrich et al. |
| 2011/0280919 A1 | 11/2011 | Moloye-Olabisi et al. |
| 2011/0282364 A1 | 11/2011 | Moloye-Olabisi et al. |
| 2013/0029030 A1 | 1/2013 | Larsen |
| 2013/0183366 A1 | 7/2013 | Saga et al. |
| 2014/0369991 A1 | 12/2014 | Schutte et al. |
| 2015/0151020 A1 | 6/2015 | Kageyama et al. |
| 2016/0120527 A1 | 5/2016 | Larsen et al. |
| 2018/0271898 A1 | 9/2018 | Basadonna et al. |
| 2020/0140625 A1 | 5/2020 | Larsen et al. |

FOREIGN PATENT DOCUMENTS

| | | |
|---|---|---|
| CN | 101239200 A | 8/2008 |
| CN | 102014973 A | 4/2011 |
| CN | 102905732 A | 1/2013 |
| CN | 105031715 A | 11/2015 |
| CN | 107126579 A | 9/2017 |
| CN | 108530671 A | 9/2018 |
| CN | 108904861 A | 11/2018 |
| DK | 73956 C | 3/1952 |

(Continued)

OTHER PUBLICATIONS

Tagaki et al. (Asian Journal of Surgery (2018), 41, 124-130).*
Office Action issued Dec. 30, 2022, in corresponding Chinese Patent Application No. 202080022290.3 (with English Translation), 7 pages.
Office Action issued Aug. 17, 2023, in Taiwanese Patent Application No. 109109252 (with English translation), 10 pages.
International Search Report issued Jun. 23, 2020 in PCT/JP2020/012251 (submitting English translation only), 2 pages.

(Continued)

*Primary Examiner* — Shirley V Gembeh
(74) *Attorney, Agent, or Firm* — Oblon, McClelland, Maier & Neustadt, L.L.P.

(57) ABSTRACT

Provided is a thrombin-carrying hemostatic sheet that is suitable for hemostasis during surgery, in particular, for hemostasis during spine surgery, that is convenient without preparation before use, and that is bioabsorbable and can be embedded in the body as it is. The hemostatic sheet is composed of a gelatin sponge carrying an effective amount of thrombin, wherein (A) the density is 30 to 55 mg/cm$^3$, and (B) the shape maintaining angle in wet conditions is 55 to 120°.

19 Claims, 2 Drawing Sheets

(56) References Cited

FOREIGN PATENT DOCUMENTS

| | | |
|---|---|---|
| JP | 58-44057 A | 3/1983 |
| JP | 3-9747 U | 1/1991 |
| JP | 6-277298 A | 10/1994 |
| JP | 8-500334 A | 1/1996 |
| JP | 2000-210376 A | 8/2000 |
| JP | 2000-510357 A | 8/2000 |
| JP | 2003-502099 A | 1/2003 |
| JP | 2005-213449 A | 8/2005 |
| JP | 3745781 B2 | 2/2006 |
| JP | 2007-9185 A | 1/2007 |
| JP | 2007-238487 A | 9/2007 |
| JP | 2008-505132 A | 2/2008 |
| JP | 2008-516736 A | 5/2008 |
| JP | 2009-183649 A | 8/2009 |
| JP | WO 2009/128474 A1 | 10/2009 |
| JP | 2010-69031 A | 4/2010 |
| JP | 2010-124931 A | 6/2010 |
| JP | 4535678 B2 | 9/2010 |
| JP | 2011-513388 A | 4/2011 |
| JP | 4769578 B2 | 9/2011 |
| JP | 2011-526544 A | 10/2011 |
| JP | 2012-95731 A | 5/2012 |
| JP | 5133061 B2 | 11/2012 |
| JP | 5191736 B2 | 2/2013 |
| JP | 2013-66536 A | 4/2013 |
| JP | 2013-523296 A | 6/2013 |
| JP | 2013-526368 A | 6/2013 |
| JP | 2013-526369 A | 6/2013 |
| JP | 5292025 B2 | 9/2013 |
| JP | 2014-5219 A | 1/2014 |
| JP | 2014-23956 A | 2/2014 |
| JP | 2014-518250 A | 7/2014 |
| JP | 2016-536042 A | 11/2016 |
| JP | 2017-531462 A | 10/2017 |
| RU | 2 545 810 C2 | 4/2015 |
| WO | WO 93/21908 A1 | 11/1993 |
| WO | WO 00/078228 A1 | 12/2000 |
| WO | WO 02/058750 A2 | 8/2002 |
| WO | WO 2006/044879 A2 | 4/2006 |
| WO | WO 2006/044882 A2 | 4/2006 |
| WO | WO 2008/019127 A2 | 2/2008 |
| WO | WO 2009/109963 A1 | 9/2009 |
| WO | WO 2012/011429 A1 | 1/2012 |
| WO | WO 2013/172472 A1 | 11/2013 |
| WO | WO 2018/165275 A1 | 9/2018 |

OTHER PUBLICATIONS

"Spongel" (registered trademark) Appended Paper (Japan), LTL Pharma Co. Ltd., 2014, 2 pages (with partial English translation).
"Highlights of Prescribing Information of RECOTHROM" (registered trademark) (USA), Baxter International Inc., 2020, 18 pages.
"Floseal" (registered trademark) Appended Paper (Japan), Baxter, 2017, 5 pages (with partial English translation).
"TACHOSIL (registered trademark) Tissue Sealing Sheet Appended paper (Japan)" CSL Limited, 2015, 20 pages (with English translation).
"TACHOSIL (registered trademark) Tissue Sealing Sheet Appended Paper Pharmaceutical Product Interview Form (Japan)" CSL, 2011, 51 pages (with partial translation).
Taiwanese Office Action issued Apr. 15, 2024 in Taiwanese Patent Application No. 109109252 (with English translation), 7 pages.
English translation of Written Opinion issued Jun. 23, 2020 in PCT/JP2020/012251, 4 pages.
Combined Chinese Office Action and Search Report issued Apr. 24, 2022 in Patent Application No. 202080022290.3 (with English language translation and English translation of Category of Cited Documents), 20 pages.
Extended European Search Report issued Nov. 9, 2022 in European Patent Application No. 20774161.2, 6 pages.
Rana Imani, et al., "Synthesis and characterization of glutaraldehyde-based crosslinked gelatin as a local hemostat sponge in surgery: An in vitro study," Bio-Medical Materials and Engineering, vol. 23, 2013, pp. 211-224.
Russian Office Action and Search Report issued Aug. 9, 2023 in Russian Patent Application No. 2021130322/14(064378) with English language translation), 31 pages.
Russian Office Action issued Feb. 20, 2024 in Russian Patent Application No. 2021130322 (with English translation), 21 pages.
Russian Office Action issued Mar. 23, 2023 in Russian Patent Application No. 2021130322/14 (with English Translation), 16 pages.

* cited by examiner

THROMBIN-CARRYING HEMOSTATIC SHEET

CROSS REFERENCE TO RELATED APPLICATIONS

This application is 371 application of International Patent Application No. PCT/JP2020/012251, filed on Mar. 19, 2020, and claims priority to Japanese Patent Application No. 2019-052339, filed on Mar. 20, 2019, both of which are incorporated herein by reference in their entireties.

TECHNICAL FIELD

The present invention relates to a hemostatic sheet carrying thrombin that has biological absorption properties and is suitable for hemostasis during a surgery, in particular, hemostasis during a spine surgery.

BACKGROUND ART

The safety of a surgery has been increased in accordance with an improvement in a surgical technique, an advancement in a surgical tool, or the like, but a hemostatic operation during hemorrhage affects the progress after the surgery, and thus, it is necessary that the hemostatic operation be accurately implemented. In general, examples of the hemostatic operation in the surgery include the compression, the ligation, the angiorrhaphy, the thermocoagulation, and the ablation of a hemorrhage area, a chemical drug, and the like. However, for example, in the field of a spine surgery with respect to a disease or a disorder according to the spine (the backbone of the head to the lower back) and the spinal nerve therein, hemorrhage from the *plexus venosus* that is intricated in the shape of a net in the spine dura mater is dominant, and it is general that the hemorrhage area is in the vicinity of an important nerve. In such a case, the hemostasis according to the thermocoagulation using a surgical tool such as an electrosurgical knife or the ablation has a high risk of damaging the nerve, and thus, is not capable of being adopted, and the hemostasis according to the ligation or the angiorrhaphy of the hemorrhage area is also difficult. For this reason, a method for performing compression hemostasis for approximately 10 minutes by using gauze very much has been generally used, but a surgical field is occupied by the gauze or the like, and thus, the subsequent surgical manipulation is hindered, and in some cases, the surgery is forced to be paused until the gauze is removed. A hemostatic material containing gelatin or collagen may be used instead of the gauze. A sponge or a sheet containing gelatin or collagen compresses the hemorrhage area in accordance with the absorption of the blood, and thus, is expected to have a hemostasis effect according to a clotting function of the absorbed blood in addition to the hemostasis of a physical function.

A gelatin sponge has high water absorption properties and high biological absorption properties. Currently, for example, Gelfoam (registered trademark) (manufactured by Pfizer Inc.) or Spongel (registered trademark) (manufactured by LTL Pharma Co., Ltd.) is commercially available as a hemostatic material including the gelatin sponge. In the section of dosage and administration of the appended paper of Spongel (registered trademark) (Non-patent literature 1), "Patch a suitable amount of Spongel to the surface of a wound on the skin or the organ in a dry state or by dipping in an isotonic sodium chloride solution or a thrombin solution, and fix Spongel by absorbing the exuded blood. This product is easily absorbed in the tissue, and thus, can be embedded in the body." is described. However, for example, in order to put the hemostatic material to the hemorrhage area having a limited space in which the hemostatic material can be used during said spine surgery, the hemostatic material is put there by being bent such that the hemostatic material can be closely attached to the hemorrhage area, but Gelfoam (registered trademark) (Thickness: approximately 7 to 10 mm) or Spongel (registered trademark) (Thickness: approximately 1 cm) is thick, and thus, is required to be sliced into the shape of a sheet that is thin to a maximum extent. In addition, in a case where the hemostatic material including the gelatin sponge described above absorbs the blood or the like, the hemostatic material is gradually expanded and softened, and thus, it may be difficult to maintain the shape. The softened hemostatic material in the shape of a sheet, for example, is bent due to a pressure at which the blood comes out in the case of performing the hemostasis with respect to eruptive hemorrhage such as an eruptive spring, which is capable of occurring in the field of the spine surgery, and thus, is not capable of being left to stand in the hemorrhage area. In addition, the hemostatic material may be applied by using tweezers to press the vicinity of the hemorrhage area while aspirating the extravasated blood with an aspirator during the hemorrhage, but the hemostatic material may be ruptured or peeled off due to the aspiration of the aspirator or the contact with the tweezers. For this reason, the manipulation of the hemostatic material including the sheet-like gelatin sponge in a wet state by absorbing the blood requires attention.

In expectation of a reduction in a hemostasis time, a method for using a gelatin sponge by being coated with or dipped in a thrombin solution that is a blood clotting agent has been known. For example, in Non-patent literature 2, the "surface of a hemorrhage area is directly coated with a solution or is coated together with a gelatin sponge having biological absorption properties" is described. However, it is necessary that the gelatin sponge containing the thrombin is prepared before using, and a complicated procedure and aseptic preparation are required. In addition, in the gelatin sponge in a wet state by the thrombin solution, the water absorption properties of the blood decrease. Further, it is difficult to maintain the shape of the gelatin sponge in a wet state by the thrombin solution or the like. For example, Spongel (registered trademark) (manufactured by LTL Pharma Co., Ltd.) and Gelfoam (registered trademark) (manufactured by Pfizer Inc.) that are a commercially available gelatin sponge are dipped the thrombin solution diluted with physiological saline, as it can be seen from pictures (FIGS. 1(*i*) and 1(*ii*)) in which the ends of each of the wet gelatin sponges are picked up with tweezers, the infiltrated sheet-like gelatin sponge is immediately bent, and thus, is not suitable for the hemostasis of the eruptive hemorrhage.

Therefore, it has been proposed to provide the gelatin sponge carrying the thrombin in a dry state (Patent literatures 1, 2, and 3). However, "in a case where a wet sponge is dried, the collapse of the sponge and/or a change in the original shape or structural integrity of a sponge material occur" and "such a change in the structure causes a reduction in the capability of the sponge material of absorbing the blood and/or the capability of the sponge of being easily fitted to the shape of the body surface" have been reported (Patent literature 3). For this reason, a gelatin sponge that is produced by a method for infiltrating only a part of the gelatin sponge, for example, only one surface of the sponge in a thrombin solution, and by freezing and drying the gelatin sponge and includes a thrombin layer only on the surface (Patent literature 3). However, the proposed gelatin sponge is thick, and it is necessary to check an applicable surface with respect to the hemorrhage area, and thus, it is difficult to paste the proposed hemostatic material to the hemorrhage area having the limited space in which the hemostatic material can be used, and there has been no report about the practical realization of the hemostatic material during a spine surgery in which the hemorrhage from the *plexus venosus* that is intricated in the shape of a net in the spine dura mater is dominant.

In order to harden the surface of the hemostatic material including the gelatin sponge, it has been proposed that gelatin sponge is highly cross-linked (Patent literature 4). For example, a method for dipping a gelatin sponge sliced to have a thickness of 0.1 mm to 10 mm in a solution in which a cross-linking agent of aldehydes such as glutaraldehyde is dissolved in alcohols, and of cross-linking the gelatin sponge has been devised. An object of such a devised method is to obtain a hemostatic material having a strength impervious to the hemorrhage, and there is no report about properties of not causing a crack even in a case where the hemostatic material is bent in a dry state, the biological absorption properties, or the like.

Floseal (registered trademark) (manufactured by Baxter International Inc.) that is an absorptive regional hemostatic material using gelled human thrombin-containing gelatin prepared by mixing granulated cross-linked gelatin and a thrombin solution has been commercially available as a hemostatic material (a kit) that can also be used in a spine surgery. In the appended paper of Floseal (Non-patent literature 3), a method for preparing a hemostatic material by using a thrombin vial, a lysate vial, a needle-tipped syringe, and a gelatin set in the kit is described, and for a foam-like hemostatic material, for example, "this product is retained in the hemorrhage area for 2 minutes by using gauze or the like that is wet with physiological saline" and "when the hemorrhage stops, an excess is gently washed and aspirated such that the formation of a clot (an amount remaining without being absorbed in the clot) is not hindered" are described. In addition, "this product is expanded after being applied up to approximately 20%, and thus, a user considers the possibility of affecting the surrounding tissues regardless of the type of surgery" and "in particular, in a case where this product is applied to a substantially closed space in the vicinity of the nerve, there is a concern that the nerve is compressed due to the expansion of this product" are described.

In addition, TachoSil (registered trademark) tissue sealing sheet (manufactured by CSL Limited) that is a tissue sealing sheet in which a sponge-like collagen sheet is used as a carrier and a thickness obtained by fixing fibrinogen and thrombin is approximately 5 mm has been commercially available. In the indication of TachoSil (registered trademark) tissue sealing sheet, a hemostasis application during a spine surgery is not included (Non-patent literature 4).

CITATION LIST

Patent Literature

[Patent literature 1] JP S58-44057 A
[Patent literature 2] WO 2009/128474
[Patent literature 3] WO 2009/109963
[Patent literature 4] JP H03-9747 U Non-Patent Literature

[Non-patent literature 1] Spongel (registered trademark) Appended Paper (Japan)

[Non-patent literature 2] HIGHLIGHTS OF PRESCRIBING INFORMATION of RECOTHROM (registered trademark) (USA)
[Non-patent literature 3] Floseal (registered trademark) Appended Paper (Japan)
[Non-patent literature 4] TachoSil (registered trademark) Tissue Sealing Sheet Appended paper (Japan)
[Non-patent literature 5] TachoSil (registered trademark) Tissue Sealing Sheet Appended Paper Pharmaceutical Product Interview Form (Japan)

SUMMARY OF INVENTION

Technical Problem

A plurality of hemostatic materials containing thrombin that have a reduced hemostasis time and are not required to be prepared before using have been already considered, but for example, there has been no report about a hemostatic sheet that is capable of being used in the hemorrhage area having the limited space in which the hemostatic material can be used during a spine surgery and is also capable of performing the hemostasis with respect to the eruptive hemorrhage yet. In addition, there is no report about the consideration of shape maintenance capability in a wet condition, a strength, expansion properties, biological absorption properties, and the like, which are suitable for the hemostatic sheet, a sheet-like hemostatic material excellent in manipulation properties, in which the above properties are considered, has been required to be developed and practically realized.

An object of the present invention is to provide a hemostatic sheet carrying an effective amount of thrombin that is suitable for hemostasis during a surgery, in particular, hemostasis during a spine surgery, has properties of not causing a crack even in a case where the hemostatic sheet in a dry state is deformed, and is less likely to be ruptured or bent even in a wet state by absorbing the blood. In addition, another object of the present invention is to provide a hemostatic sheet that has low expansion properties and is comparatively promptly biologically absorbed even in a case where a surgery is ended in a state in which the hemostatic sheet is closely attached to a hemorrhage area in order to prevent re-hemorrhage.

Solution to Problem

In such a circumstance, the present inventors have conducted intensive studies in order to develop a hemostatic sheet including a gelatin sponge carrying thrombin that has properties such as properties of not causing a crack even in a case where a hemostatic sheet in a dry state is deformed in order to be closely attached to a hemorrhage area, shape maintenance capability in which the hemostatic sheet in a wet state by absorbing the blood is impervious to eruptive hemorrhage, properties in which swelling properties after blood infiltration are not high, and biological absorption properties.

As a result thereof, it has been found that in order to provide the hemostatic sheet including the gelatin sponge carrying the thrombin that has the properties of not causing a crack even in a case where the hemostatic sheet in a dry state is bent and has the shape maintenance capability impervious to the hemostasis even in the eruptive hemorrhage, it is necessary that the hemostatic sheet has a constant density and is in a range of the shape maintenance capability during the infiltration, and thus, the present invention has been completed.

In addition, it has found that in order to provide the hemostatic sheet including the gelatin sponge carrying the thrombin that has low expansion properties and the properties of being comparatively promptly biologically absorbed, in addition to the properties described above, it is necessary that the hemostatic sheet has a constant density and is in the range of the shape maintenance capability during the infiltration, and thus, the present invention has been completed.

Further, it has been found that in order to obtain the hemostatic sheet including the gelatin sponge carrying the thrombin that has the properties described above, it is preferable that the gelatin sponge is a thermally cross-linked gelatin sponge that is thermally cross-linked by a specific production method, and thus, the present invention has been completed.

That is, the present invention relates to:

[1] a hemostatic sheet including a gelatin sponge carrying an effective amount of thrombin, in which A) the hemostatic sheet has a density of 30 to 55 mg/cm$^3$, and B) when the sheet cut to have a length of 10.0±1.0 mm and a breadth of 20.0±1.0 mm is dipped in physiological saline for 30 minutes, and then, is placed on a horizontally retained cylindrical metal rod having a diameter of 2.0±0.2 mm and a length of greater than or equal to 11.0 mm such that a center line of the sheet in the breadth direction is coincident with the rod, and is left to stand for 5 to 30 seconds, a shape maintaining angle in a wet condition, represented by a spread angle between both ends of the sheet (innermost ends) centered on the metal rod, is 55 to 120 degrees;

[2] the hemostatic sheet according to [1], in which the hemostatic sheet has a thickness in a range of 1.0 to 3.5 mm;

[3] the hemostatic sheet according to [1] or [2], in which the hemostatic sheet has water absorption properties of absorbing 0.1 mL of a phosphate buffer solution dropped on the sheet cut to have a length and a breadth of 10.0±1.0 mm within 10 seconds;

[4] the hemostatic sheet according to any one of [1] to [3], in which when the hemostatic sheet according to any one of [1] to [3], cut to have a weight of 50.0±2.5 mg, is put in a conical flask containing a pepsin-hydrochloric acid test solution (80000±8000 U/100 mL), and the conical flask is shaken at a velocity at which an aqueous surface of the pepsin-hydrochloric acid test solution shakes, in a constant-temperature water bath set at 37±1° C., a disappearance time when a residue of the hemostatic sheet is not visually observed is shorter than 330 minutes;

[5] the hemostatic sheet according to any one of [1] to [4], in which the hemostatic sheet is a hemostatic sheet including a gelatin sponge carrying 10 to 200 IU/cm$^2$ of human recombinant thrombin;

[6] the hemostatic sheet according to any one of [1] to [5], in which the hemostatic sheet is a hemostatic sheet including a gelatin sponge carrying 50±15 IU/cm$^2$ of the human recombinant thrombin;

[7] the hemostatic sheet according to any one of [1] to [6], in which the shape maintaining angle in a wet condition according to [1] is 64 to 100 degrees;

[8] the hemostatic sheet according to any one of [1] to [7], in which the density is 35 to 55 mg/cm$^3$;

[9] the hemostatic sheet according to any one of [1] to [8], in which the density is 37 to 52 mg/cm$^3$;

[10] the hemostatic sheet according to any one of [4] to [9], in which the disappearance time according to [4] is shorter than 300 minutes;

[11] the hemostatic sheet according to any one of [1] to [10], in which the hemostatic sheet is for hemostasis during a spine surgery;

[12] a hemostatic sheet including a gelatin sponge carrying 10 to 200 IU/cm$^2$ of human recombinant thrombin, for being used in hemostasis during a spine surgery, in which A) the hemostatic sheet has a thickness in a range of 1.0 to 3.5 mm, B) the hemostatic sheet has a density of 30 to 55 mg/cm$^3$, C) the hemostatic sheet has water absorption properties of observing 0.1 mL of a phosphate buffer solution dropped on the sheet cut to have a length and a breadth of 10.0±1.0 mm within 10 seconds, and D) when the sheet cut to have a length of 10.0±1.0 mm and a breadth of 20.0±1.0 mm is dipped in physiological saline for 30 minutes, and then, is placed on a horizontally retained cylindrical metal rod having a diameter of 2.0±0.2 mm and a length of greater than or equal to 11.0 mm such that a center line of the sheet in the breadth direction is coincident with the rod, and is left to stand for 5 to 30 seconds, a shape maintaining angle in a wet condition, represented by a spread angle between both ends of the sheet (innermost ends) centered on the metal rod, is 55 to 120 degrees;

[13] a hemostatic sheet including a gelatin sponge carrying 50±15 IU/cm$^2$ of human recombinant thrombin, for being used in hemostasis during a spine surgery, in which A) the hemostatic sheet has a thickness in a range of 1.0 to 3.5 mm, B) the hemostatic sheet has a density of 30 to 55 mg/cm$^3$, C) the hemostatic sheet has water absorption properties of absorbing 0.1 mL of a phosphate buffer solution dropped on the sheet cut to have a length and a breadth of 10.0±1.0 mm within 10 seconds, and D) when the sheet cut to have a length of 10.0±1.0 mm and a breadth of 20.0±1.0 mm is dipped in physiological saline for 30 minutes, and then, is placed on a horizontally retained cylindrical metal rod having a diameter of 2.0±0.2 mm and a length of greater than or equal to 11.0 mm such that a center line of the sheet in the breadth direction is coincident with the rod, and is left to stand for 5 to 30 seconds, a shape maintaining angle in a wet condition, represented by a spread angle between both ends of the sheet (innermost ends) centered on the metal rod, is 55 to 120 degrees;

[14] the hemostatic sheet according to any one of [1] to [13], in which the hemostatic sheet substantially contains no cross-linking agent;

[15] a hemostatic sheet including a gelatin sponge carrying 50±15 IU/cm$^2$ of human recombinant thrombin and substantially containing no cross-linking agent, for being used in hemostasis during a spine surgery, in which A) the hemostatic sheet has a thickness in a range of 1.0 to 3.5 mm, B) the hemostatic sheet has a density of 30 to 55 mg/cm$^3$, C) the hemostatic sheet has water absorption properties of absorbing 0.1 mL of a phosphate buffer solution dropped on the sheet cut to have a length and a breadth of 10.0±1.0 mm within 10 seconds, and D) when the sheet cut to have a length of 10.0±1.0 mm and a breadth of 20.0±1.0 mm is dipped in physiological saline for 30 minutes, and then, is placed on a horizontally retained cylindrical metal rod having a diameter of 2.0±0.2 mm and a length of greater than or equal to 11.0 mm such that a center line of the sheet in the breadth direction is coincident with the rod, and is left to stand for 5 to 30 seconds, a shape maintaining angle in a wet condition, represented by a spread angle between both ends of the sheet (innermost ends) centered on the metal rod, is 55 to 120 degrees;

[16] the hemostatic sheet according to any one of [1] to [15], in which the gelatin sponge is a thermally cross-linked gelatin sponge;

[17] the hemostatic sheet according to [16], in which the thermally cross-linked gelatin sponge is produced by performing a thermal treatment with respect to a gelatin sponge obtained by foaming and drying 3 to 6 weight % of a gelatin solution to have a foam density of 0.20 to 0.34 g/mL, at a temperature of 120 to 165° C. for 10 to 30 hours in total;

[18] the hemostatic sheet according to any one of [1] to [17], including the gelatin sponge carrying an effective amount of thrombin, in which the hemostatic sheet is produced by a production method including: (1) a step of producing a thermally cross-linked gelatin sponge by performing a thermal treatment with respect to a gelatin sponge obtained by foaming and drying 3 to 6 weight % of a gelatin solution to have a foam density of 0.20 to 0.34 g/mL, at a temperature of 120 to 165° C. for 10 to 30 hours in total; and (2) a step of producing a cross-linked gelatin sponge carrying an effective amount of thrombin by infiltrating the thermally cross-linked gelatin sponge obtained in the step (1) in a thrombin solution, and then, by drying the gelatin sponge, and the dried gelatin sponge or the thermally cross-linked gelatin sponge obtained in the step (1), or the cross-linked gelatin sponge carrying an effective amount of thrombin, obtained in the step (2), is sliced to have a thickness of 1.0 to 3.5 mm;

[19] a method for producing a hemostatic sheet including a gelatin sponge carrying an effective amount of thrombin, the method including: (1) a step of producing a thermally cross-linked gelatin sponge by performing a thermal treatment with respect to a gelatin sponge obtained by foaming and drying 3 to 6 weight % of a gelatin solution to have a foam density of 0.20 to 0.34 g/mL, at a temperature of 120 to 165° C. for 10 to 30 hours in total; and (2) a step of producing a cross-linked gelatin sponge carrying an effective amount of thrombin by infiltrating the thermally cross-linked gelatin sponge obtained in the step (1) in a thrombin solution, and then, by drying the gelatin sponge, in which the dried gelatin sponge or the thermally cross-linked gelatin sponge obtained in the step (1), or the cross-linked gelatin sponge carrying an effective amount of thrombin, obtained in the step (2), is sliced to have a thickness of 1.0 to 3.5 mm; and

[20] a method for performing hemostasis with respect to hemorrhage of a patient during a spine surgery, by using the hemostatic sheet according to any one of [1] to [18].

Advantageous Effects of Invention

According to the present invention, it is possible to provide a hemostatic sheet including a gelatin sponge carrying thrombin that has properties of not causing a crack even in a case where the hemostatic sheet in a dry state is bent and has shape maintenance capability impervious to hemostasis even in eruptive hemorrhage.

In addition, it is possible to provide a hemostatic sheet including a gelatin sponge carrying thrombin that has low expansion properties and properties of being comparatively promptly biologically absorbed.

In addition, it is possible to provide a hemostatic sheet including a thermally cross-linked gelatin sponge carrying thrombin that has properties of not causing a crack even in a case where the hemostatic sheet in a dry state is bent, has shape maintenance capability impervious to hemostasis even in eruptive hemorrhage, has low expansion properties, and has properties of being comparatively promptly biologically absorbed.

In addition, it is possible to provide a method for producing a hemostatic sheet including a gelatin sponge carrying thrombin that has properties of not causing a crack even in a case where the hemostatic sheet in a dry state is bent and has shape maintenance capability impervious to hemostasis even in eruptive hemorrhage.

In addition, it is possible to provide a method for performing hemostasis with respect to hemorrhage of a patient during a spine surgery, by using a hemostatic sheet including a gelatin sponge carrying thrombin that has properties of not causing a crack even in a case where the hemostatic sheet in a dry state is bent and has shape maintenance capability impervious to hemostasis even in eruptive hemorrhage.

DESCRIPTION OF EMBODIMENTS

Figure 1:
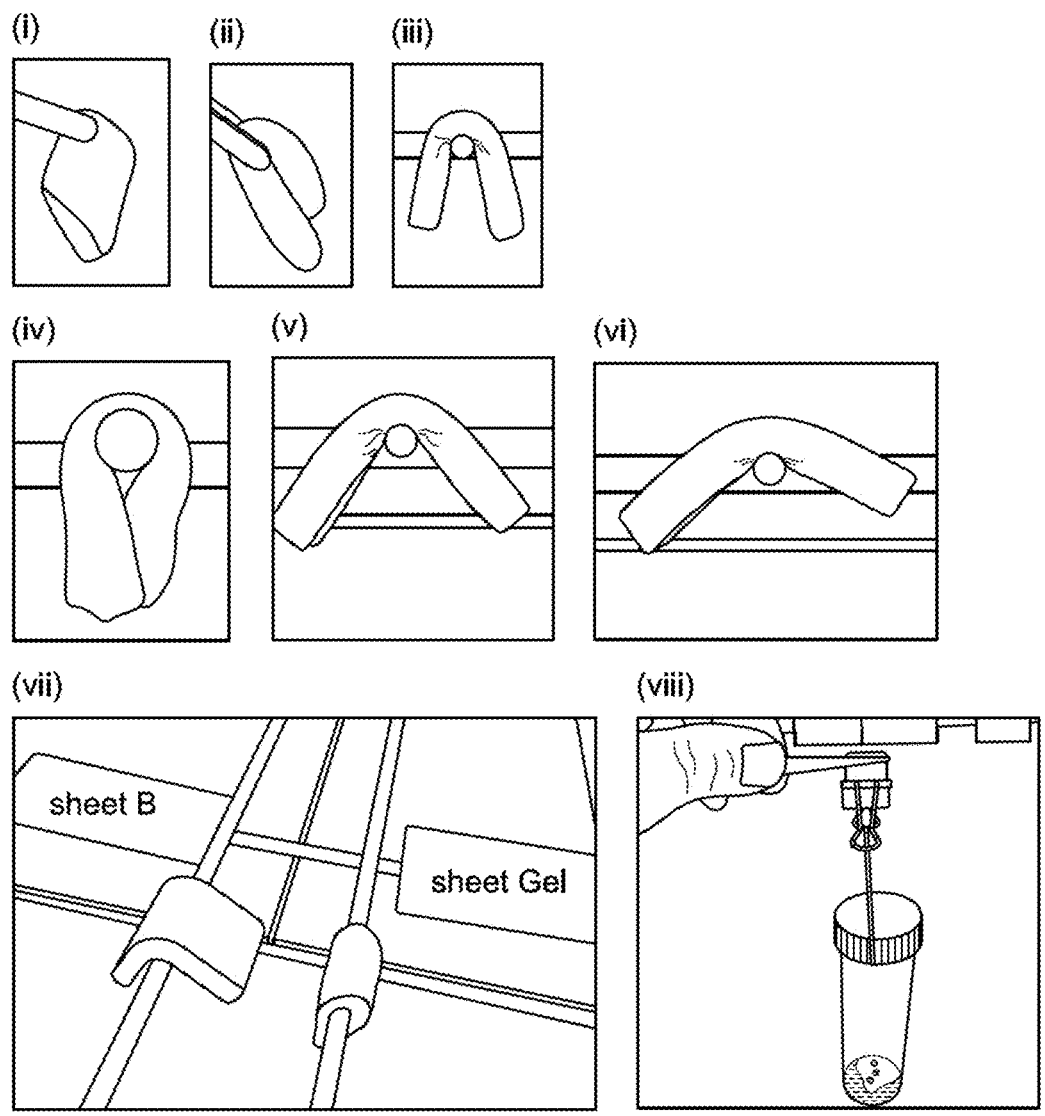
FIG. 1 is a picture, in which (i) and (ii) are pictures illustrating a state in which Spongel (registered trademark) (manufactured by LTL Pharma Co., Ltd.) and Gelfoam (registered trademark) (manufactured by Pfizer Inc.) are wet with a thrombin solution described in the background art, respectively, (iii), (iv), (v), and (vi) are pictures of a sheet Spo, a sheet Gel, a sheet B, and a sheet F, which are imaged in order to measure a shape maintaining angle in a wet condition, in (3-1) of Example 3, respectively, (vii) is a picture of a test system appearance for describing a test method of shape maintenance capability in a wet condition, in (3-1) of Example 3, and (viii) is a picture of a test system appearance for describing a measurement method of a tensile strength, in (3-3) of Example 3.

The present invention relates to a hemostatic sheet (hereinafter, may be referred to as the "hemostatic sheet of the present invention") including a gelatin sponge carrying an effective amount of thrombin. As an aspect, the hemostatic sheet of the present invention relates to a hemostatic sheet during a spine surgery.

Herein, the "gelatin sponge" indicates a gelatin sponge in which gelatin is processed into the shape of a sponge having a porous structure. The gelatin that is used as a raw material is not particularly limited insofar as the gelatin can be used as a medicinal product, and animal-derived gelatin, for example, medical gelatin produced from beef bones, pig hide, or the like can be used. As a processing method, for example, a gelatin solution is foamed, and the foam is frozen and dried, and thus, a gelatin sponge is prepared.

The "thrombin" that is used in the present invention is one of enzymes involved in a blood clotting mechanism, and has properties of hydrolyzing fibrinogen. The thrombin that is used in the present invention is not particularly limited insofar as the thrombin can be applied by being carried on the gelatin sponge, and for example, thrombin listed in The Japanese Pharmacopoeia, Seventeenth Edition (bovine or human-derived thrombin) or RECOTHROM that is human recombinant thrombin (registered trademark) (manufactured by Baxter International Inc.) can be used.

Herein, the "effective amount of thrombin" indicates the amount of thrombin having excellent hemostasis capability, and a suitable amount according to each thrombin can be set. For example, in consideration of the hemostatic sheet of the present invention using the human recombinant thrombin, a hemostasis effect is checked in a freeze-dried gelatin sponge carrying approximately 50 IU/cm$^2$ of thrombin, and thus, a carried amount of the effective amount of thrombin, for example, can be 10 to 200 IU/cm$^2$, can be 30 to 80 IU/cm$^2$ as an aspect, and can be 50±15 IU/cm$^2$ as an aspect. Note that, the upper limit and the lower limit thereof can be arbitrarily combined, as desired. Examples of a method for quantitating the thrombin include a quantitative method described in The Japanese Pharmacopoeia.

Herein, "hemostatic" indicates being applied to a hemorrhage area, and for example, performing hemostasis with respect to the exuded or erupted blood.

Herein, a "sheet", "sheet-like", or a "sheet carrier" indicates an object or a shape having a two-dimensional extent, or a substance to be a base for fixing the other substance, which has a thickness of approximately 0.2 to 5.0 mm and can be bent or rounded.

Herein, the "hemostatic sheet" indicates a hemostatic material having a thickness of approximately 0.2 to 5.0 mm. The hemostatic sheet is applied to the hemorrhage area, and performs hemostasis by a method for absorbing and/or fixing the exuded or erupted blood. A length and a breadth are arbitrary, and a size that is easily used in a clinical site (for example, a strip-like sheet having a length of 8.0 mm and a breadth of 12.0 mm, a square sheet having a length and a breadth of 20.0 mm, a rectangular sheet having a length of 10.0 mm and a breadth of 20.0 mm, and the like) can be suitably adopted. In addition, the hemostatic sheet can be used by being cut to have a size suitable in use. Note that, the surface of the hemostatic sheet has a length and a breadth, and a longer side is defined as the breadth. In addition, the breadth may be described as a width.

The "thickness" is a length of the object having a two-dimensional extent in a perpendicular direction with respect to the extent. Examples of a method for measuring the thickness of the hemostatic sheet of the present invention include a method for imaging the surface of the hemostatic sheet in the perpendicular direction and for measuring the thickness on an imaging screen, or a method for measuring the thickness by using a caliper. In the thickness of the hemostatic sheet of the present invention, it is necessary to consider that the hemostatic sheet is also applied to the hemorrhage of the spine dura mater that occurs in a narrow surgical site, in a spine surgery. In a method for producing the hemostatic sheet of the present invention, the thickness may be slightly changed due to a production variation, but the thickness can be approximately homogeneous in a range of 1.0 to 3.5 mm as an aspect, in a range of 1.5 to 3.3 mm as an aspect, and in a range of 2.0 to 3.2 mm as an aspect.

The "density" is a mass (a weight) per unit volume. Examples of a method for measuring the density of the hemostatic sheet include a method for dividing the mass (the weight) of the hemostatic sheet by a volume calculated by measuring the length, the breadth, and the thickness of the hemostatic sheet with a caliper or the like, and by multiplying the length, the breadth, and the thickness together. It is preferable that the hemostatic sheet has a certain degree of deformation tolerance from the viewpoint of being applied to the hemorrhage area, and in a case where the density excessively increases, there is a possibility that a crack or the like occurs due to deformation. On the other hand, in order to have shape maintenance capability in a wet condition, a certain degree of density is required. The density at which the hemostatic sheet carrying the thrombin according to the present invention has the deformation tolerance can be 25 to 55 mg/cm$^3$ as an aspect, can be 30 to 55 mg/cm$^3$ as an aspect, can be 35 to 55 mg/cm$^3$ as an aspect, can be 37 to 52 mg/cm$^3$ as an aspect, and can be 38 to 45 mg/cm$^3$ as an aspect. Note that, the upper limit and the lower limit thereof can be arbitrarily combined, as desired. In addition, in the upper limit and the lower limit thereof, the upper limit can be an arbitrary value of 45 to 55 mg/cm$^3$, and the lower limit can be an arbitrary value of 25 to 38 mg/cm$^3$, as desired.

Herein, the "water absorption properties", for example, indicate properties of absorbing a liquid such as a phosphate buffer solution, physiological saline, water, and the blood. When the hemostatic sheet of the present invention having a thickness in a range of 1.0 to 3.5 mm is applied to the hemorrhage area, it is desirable that the hemostatic sheet promptly absorbs the liquid from the viewpoint that the hemostatic sheet is closely attached to the hemorrhage area by absorbing the blood, and a hemostasis function of the thrombin is exhibited. Examples of an evaluation method of the water absorption properties, specifically, include a method for dropping 0.1 mL of a phosphate buffer solution on one surface of the hemostatic sheet of the present invention that has a thickness in a range of 1.0 to 3.5 mm and is cut into the shape of a square having a length and a breadth of 10.0±1.0 mm, and for measuring a time until the liquid on the hemostatic sheet of the present invention is not capable of being visually checked. According to the method described above, prompt water absorption properties, for example, can be within 10 seconds as an aspect, can be within 5 seconds as an aspect, can be within 2 seconds as an aspect, and can be within 1 second as an aspect.

Herein, the "shape maintaining angle in a wet condition" indicates a spread angle between both ends of the sheet (innermost end) that is measured by a shape maintenance capability test in a wet condition. The shape maintenance capability test in a wet condition is defined as a test for measuring the shape maintaining angle in a wet condition when the hemostatic sheet of the present invention that has a thickness in a range of 1.0 to 3.5 mm and is cut to have a length of 10.0±1.0 mm and a breadth of 20.0±1.0 mm is dipped in physiological saline for 30 minutes, and then, is placed on a horizontally retained cylindrical metal rod having a diameter of 2.0±0.2 mm and a length of greater than or equal to 11.0 mm such that a center line of the sheet in the breadth direction (that is, a center line for dividing the rectangular sheet into two square sheets having a length of 10.0±1.0 mm and a breadth of 10.0±1.0 mm) is coincident with the rod, and is left to stand for 5 to 30 seconds as an aspect, and for 30 seconds as an aspect. In a case where the shape maintaining angle in a wet condition is small (that is, both ends of the sheet are in a state of hanging down), the shape maintenance capability in a wet condition is low, and in a case where the shape maintaining angle in a wet condition is large (that is, both ends of the sheet are in a state of being opened), the shape maintenance capability in a wet condition is high. As described in Example 5 described below, it is preferable that the shape of the sheet after a wet state with the blood or the like is maintained to a certain degree, from the viewpoint of manipulation properties during hemostasis. The shape maintaining angle in a wet condition at which the hemostatic sheet of the present invention wet with the blood or the like is impervious to a hemostatic operation or eruptive hemorrhage can be 55 to 120 degrees as an aspect, can be 60 to 120 degrees as an aspect, can be 62 to 110 degrees as an aspect, can be 64 to 110 degrees as an aspect, can be 64 to 100 degrees as an aspect, can be 68 to 110 degrees as an aspect, and can be 68 to 88 degrees as an aspect. Note that, the upper limit and the lower limit thereof can be arbitrarily combined, as desired.

Herein, the "tensile strength" indicates a maximum tensile load (g) that is not ruptured by adding a tensile force to the hemostatic sheet of the present invention in a vertical direction or a horizontal direction. Examples of a method for measuring the tensile strength, specifically, include a method for infiltrating the hemostatic sheet of the present invention that has a thickness in a range of 1.0 to 3.5 mm and is cut into the shape of a square having a length and a breadth of 15.0±1.0 mm in physiological saline for 60 minutes, for fixing one end of the sheet while clamping the end with an instrument such as tweezers, for applying a constant load to the other end in a vertical direction, for measuring a load until a rupture occurs (n=3), for measuring a load at which a rupture does not occur over the entire sheet a plurality of times, and for calculating an average value. Note that, in this method, in the determination of the presence or absence of a rupture, a case where a load is applied to the sheet and the sheet is not ruptured for 5 seconds is defined as no rupture, and a case where a load is applied to the sheet and the sheet is ruptured within 5 seconds is defined as a rupture. In this method, a preferred tensile strength at which the hemostatic sheet impervious to the hemostatic operation or the eruptive hemorrhage even after absorbing the blood can be greater than or equal to 20 g as an aspect, can be greater than or equal to 22 g as an aspect, can be greater than or equal to 29 g as an aspect, can be 20 g to 40 g as an aspect, and can be 22 g to 35 g as an aspect. Note that, the upper limit and the lower limit thereof can be arbitrarily combined, as desired.

Herein, the "biological absorption properties" indicate properties in which the hemostatic sheet of the present invention disappears in the biological body. In general, in a case where the hemostatic material such as a gelatin sponge remains in the body for a long period of time, a risk of inducing granuloma or the like increases, and thus, it is desirable that the hemostatic sheet has biological absorption properties in which the hemostatic sheet can be embedded in the body or has high biological absorption properties, that is, the hemostatic sheet that has finished the function as the hemostatic material promptly disappears. Examples of a method for evaluating the biological absorption properties include a test using the liver of a rat. Specifically, the test is a method for pressing a plate for creating a damage with a hole having a diameter of 8 mm against the liver surface of a male rat, for cutting a protruding portion by a surgical knife such that hemorrhage occurs, for applying the hemostatic sheet of the present invention that is cut into the shape of a square having a length and a breadth of approximately 5 mm and has a thickness in a range of 1.0 to 3.5 mm to the hemorrhage area, for suturing a laparotomy site after checking that re-hemorrhage is not observed, for performing the laparotomy again after a constant period elapses, and for checking the disappearance of the hemostatic sheet of the present invention by visual observation. It is desirable that a disappearance moment of the hemostatic sheet of the present invention is the same time as or earlier than that of a commercially available hemostatic material having biological absorption properties. In Pharmaceutical Product Interview Form of TachoSil (registered trademark) (Non-patent literature 5), "Patch TachoComb of 0.5 cm×0.5 cm/head (syncopation) to a wounded surface of the liver of a male rat, and perform visual observation with time" and "TachoComb disappeared in all examples (syncopation) after 20 weeks from the patch" are described, and thus, for example, in the test, it is desirable that the moment at which a disappearance example of the hemostatic sheet of the present invention is checked is shorter than or equal to 20 weeks as an aspect, is shorter than or equal to 18 weeks as an aspect, is shorter than or equal to 14 weeks as an aspect, is shorter than or equal to 12 weeks as an aspect, is shorter than or equal to 10 weeks as an aspect, and is shorter than or equal to 8 weeks as an aspect. Note that, the lower limit of the moment at which the disappearance example is checked is 1 day.

Examples of another method for evaluating the biological absorption properties include a test using a pepsin-hydrochloric acid test solution. The pepsin is one of aspartic proteases, and the gelatin disappears by being decomposed with the protease. For this reason, the test is capable of evaluating the ease of disappearance of the hemostatic sheet of the present invention, including the gelatin sponge. Specifically, the test is a method for applying the hemostatic sheet of the present invention that has a thickness in a range of 1.0 to 3.5 mm, has a weight of 50±2.5 mg, and is cut into the shape of a square to a conical flask of 200 mL containing the pepsin-hydrochloric acid test solution (a test solution prepared by containing 80000±8000 U of the pepsin in 100 mL), for shaking the conical flask in a constant-temperature water bath set at a temperature of 37±1° C., and for determining a time (minute) when the residue of the sheet is not observed (hereinafter, may be referred to as a disappearance time) by visual observation. Note that, a shaking velocity is not particularly limited insofar as the velocity is suitably selected as a velocity at which the aqueous surface of the test solution shakes, and specifically, for example, it is preferable that the shaking velocity is 78 times/minute at the time of using a desktop type shaking constant-temperature bath WATER BATH SHAKER PERSONAL-11 that is a constant-temperature water bath manufactured by TAITEC Corporation. In a case where the disappearance time is longer than or equal to a constant period of time, high biological absorption properties are not capable of being expected. The disappearance time is shorter than 330 minutes as an aspect, is shorter than 300 minutes as an aspect, and is shorter than 200 minutes as an aspect. Note that, the lower limit of the disappearance time is 1 minute.

Examples of another method for evaluating the biological absorption properties include a method for putting the hemostatic sheet of the present invention that has a thickness in a range of 1.0 to 3.5 mm and is cut to have a suitable size in cell fluid in which macrophage or the like that is phagocyte is cultured or isolated, for storing the hemostatic sheet in a constant-temperature bath set at a temperature of approximately 37° C., and for checking the disappearance time of the sheet.

Herein, the "deformation tolerance" indicates that a crack or a rupture does not occur when the hemostatic sheet of the present invention after being dried is pushed and bent. Examples of a method for evaluating the deformation tolerance include a method for checking the presence or absence of a crack or a rupture of the sheet with visual observation when the hemostatic sheet of the present invention that has a thickness in a range of 1.0 to 3.5 mm and is cut to have a length of approximately 10 mm and a breadth of approximately 20 mm is pushed and bent such that the breadth of the sheet is wound around a cylindrical curved surface that is a lateral surface of a tube having a diameter of approximately 7 mm, as an aspect.

Herein, the "expansion of the hemostatic sheet" indicates that the length, the breadth, and/or the thickness of the hemostatic sheet of the present invention are increased by the infiltration. When the hemostatic sheet is embedded in the body in a state of being applied to the hemorrhage area by being used in the hemostasis during a spine surgery, a risk of compressing the surrounding tissues, the nerve, or the like is low in a case where an expansion rate is small, and thus, the hemostatic sheet may not be removed after the hemostasis. As a measurement method of the expansion rate of the hemostatic sheet of the present invention, for example, as an aspect, the hemostatic sheet of the present invention is cut into the shape of a square in a range of 10.0±0.5 mg, is infiltrated in a petri dish containing purified water, an image of the hemostatic sheet at a time point when 0 hours, 1 hour, 3 hours, and/or 6 hours elapses after the infiltration is obtained by imaging the lateral surface of the hemostatic sheet with a microscope or the like (a magnification of 10 times), the length of one side of the hemostatic sheet, and the thickness are measured on the image, and a change rate with respect to a wet state is calculated from the length of one side of the hemostatic sheet and the thickness before the infiltration to be a swelling rate. The upper limit of the expansion rate of the hemostatic sheet of the present invention is less than 15% as an aspect, is less than 10% as an aspect, is less than 5% as an aspect, and is less than 3% as an aspect. Note that, the thickness of the hemostatic sheet of the present invention can be decreased in accordance with an increase in the own weight due to a wet state, and thus, the lower limit of the expansion rate of the hemostatic sheet of the present invention is greater than or equal to −15% as an aspect, and is greater than or equal to −10% as an aspect.

It is preferable that the hemostatic sheet of the present invention is a sheet having a shape maintaining angle in a wet condition, imparting excellent hemostasis capability, and suitable biological absorption properties together. As an aspect, the hemostatic sheet is a hemostatic sheet in which a shape maintaining angle in a wet condition is 55 to 120 degrees, and in a test using a pepsin-hydrochloric acid test solution, a disappearance time is shorter than 330 minutes. As an aspect, the hemostatic sheet is a hemostatic sheet in which a shape maintaining angle in a wet condition is 60 to 120 degrees, and in a test using a pepsin-hydrochloric acid test solution, a disappearance time is shorter than 300 minutes. As an aspect, the hemostatic sheet is a hemostatic sheet in which a shape maintaining angle in a wet condition is 62 to 110 degrees, and in a test using a pepsin-hydrochloric acid test solution, a disappearance time is shorter than 300 minutes. As an aspect, the hemostatic sheet is a hemostatic sheet in which a shape maintaining angle in a wet condition is 64 to 110 degrees, and in a test using a pepsin-hydrochloric acid test solution, a disappearance time is shorter than 300 minutes. Note that, the upper limit and the lower limit of the shape maintaining angle in a wet condition can be arbitrarily combined, as desired. In addition, the shape maintaining angle in a wet condition, and the disappearance time in the test using the pepsin-hydrochloric acid test solution can be arbitrarily combined, as desired.

Herein, the "spine surgery" indicates a spine surgery with respect to a disease or a disorder according to the spine (the backbone of the head to the lower back) and the spinal nerve therein, and hemorrhage from the *plexus venosus* that is intricated in the shape of a net in the spine dura mater is dominant as the hemorrhage in the surgery, and but the hemorrhage is not limited thereto. The hemostatic operation is often required in a narrow surgical site of approximately several mm to dozen mm. Examples of the spine surgery are capable of including articular inflammation, degeneration of the intervertebral disk, dorsalgia, lumbago, sciatica, cervical spondylosis, neck pain, kyphotic deformity, rachioscoliosis, degenerative arthropathy, arthrosis deformans, spondylolysis, spondylolisthesis, intervertebral disc extrusion, spinal instability, and the like.

The gelatin sponge used in the present invention may further carry various pharmaceutical additives, as desired, in a range in which a desired effect of the present invention can be attained. Such pharmaceutical additives are not particularly limited insofar as the pharmaceutical additives are pharmaceutically allowed and pharmacologically allowed. For example, the gelatin sponge is capable of carrying a stabilizing agent, a softening agent, a penetrating agent, and the like.

Examples of the stabilizing agent are capable of including alcohols such as polyol, glycerol, and polyethylene glycol, sugar/sugar alcohols such as glucose, saccharose, and sorbitol, polyalkylene glycol, amino acids, and the like.

Examples of the softening agent are capable of including polyethylene glycol, glycerin, and the like.

Examples of the penetrating agent are capable of including a surfactant such as polysorbate 80, and the like.

The gelatin sponge is capable of suitably carrying a suitable amount of one type of the pharmaceutical additives or a combination of two or more types thereof.

The gelatin sponge used in the present invention may further carry other active components, as desired, in a range in which a desired effect of the present invention can be attained. Examples of the active components are capable of including fibrinogen, vitamin K-dependent clotting factor, factor XIII, fibronectin, an antibacterial agent, an anti-inflammatory agent, and/or a combination thereof, but the active components are not limited thereto.

Herein, the "cross-linked gelatin sponge" or the "gelatin sponge that is cross-linked" indicates a gelatin sponge subjected to a cross-linking treatment. The cross-linking treatment is not particularly limited insofar as the cross-linking treatment finally imparts the characteristic as the gelatin sponge that can be used in the hemostatic sheet of the present invention. For example, a desired cross-linking treatment can be performed by thermal cross-linkage for performing a thermal treatment or chemical cross-linkage according to the use of a cross-linking agent (for example, formaldehyde, glutaraldehyde, carbodiimide, ethylene glycol diglycidyl ether, polyethylene glycol diglycidyl ether, hexamethylene diisocyanate, epoxies, and the like). An ε-amino group of a Lys residue of the gelatin becomes an aldehyde group through oxidation·deamidation in molecules or between molecules by a thermal treatment, and the thermal cross-linkage of the gelatin is caused by condensation between a reactive group thereof and an ε-amino group of another Lys residue. Molecular mobility decreases in accordance with the cross-linkage, and thus, for example, a cross-linking degree can be evaluated by measuring an extension in a relaxation time with solid-state NMR. Note that, the cross-linked gelatin sponge by the thermal cross-linkage may be referred to as a "thermally cross-linked gelatin sponge", and the cross-linked gelatin sponge by the cross-linking agent may be referred to as a "chemical cross-linked gelatin sponge". Note that, the "cross-linked gelatin sponge", the "gelatin sponge that is cross-linked", the "thermally cross-linked gelatin sponge", and the "chemical cross-linked gelatin sponge" can be directly applied to the description of the hemostatic sheet of the present invention.

An aspect of the cross-linking treatment is the thermal cross-linkage. Herein, the thermal cross-linkage will be described as a thermal treatment. It is reported that not only glutaraldehyde but also many cross-linking agents are not sufficient in biological compatibility, and remaining properties and toxicity thereof are concerned, in the literature or the like (van Luyn M J., Biomaterials, 13(14), pp. 1017-1024 (1992): van Luyn M J., J. Biomed., Mater. Res., 26(8), pp. 1091-1110 (1992): Huang Lee L L., J. Biomed. Mater. Res., 24(9), pp. 1185-1201 (1990) or the like). As an aspect of the gelatin sponge of the present invention, the gelatin sponge does not substantially contain the cross-linking agent. Note that, in the present invention, "not substantially containing the cross-linking agent" indicates that an embodiment of adding the cross-linking agent is also included in the present invention, within a range not impairing the object of the present invention, in particular, within a range in which the toxicity is not exhibited.

Herein, the "foam density" is a value (unit: g/mL) obtained by weighing a predetermined content of gelatin foam from gelatin foam obtained by foaming a gelatin solution with cooling, stirring, and the like, by measuring a mass thereof, and by dividing the mass by the content.

The present invention also relates to a method for producing a hemostatic sheet.

The description of the hemostatic sheet of the present invention can be directly applied to the "gelatin sponge", the "thrombin", the "effective amount of thrombin", "hemostatic", the "sheet", "sheet-like", the "sheet carrier", the "hemostatic sheet", the "thickness", the "density", the "water absorption properties", the "shape maintaining angle in a wet condition", the "spine surgery", the "thermally cross-linked gelatin sponge", and the "foam density" of the present invention, which are used in the method for producing the hemostatic sheet. In addition, the description of the method for producing the hemostatic sheet of the present invention can be directly applied to the hemostatic sheet of the present invention.

The method for producing the hemostatic sheet of the present invention will be described below.

(1) Production of Hemostatic Sheet Carrier Using Cross-Linked Gelatin Sponge

The gelatin solution is prepared by dissolving gelatin. The gelatin solution can be prepared by adding animal-derived gelatin to purified water heated to approximately 37 to 53° C. such that a concentration thereof is 4 to 6 weight % as an aspect, is 4 to 5 weight % as an aspect, and is 3.8 to 4.5 weight % as an aspect, and by performing stirring until the gelatin is completely dissolved. Note that, the upper limit and the lower limit thereof can be arbitrarily combined, as desired.

Gelatin foam having a desired foam density is prepared by foaming the gelatin solution with cooling and stirring. As an aspect, the gelatin solution is put in a hopper of a continuous stirrer, and then, a constant amount of gelatin solution is supplied to a stirring unit and the air is also fed into the solution, foaming is performed by performing stirring while performing cooling to approximately 20 to 23° C., and thus, gelatin foam having a foam density in a range of 0.25 to 0.34 g/mL is obtained. The concentration and the foam density of the gelatin solution can be suitably selected in accordance with a condition, and the gelatin foam is gelatin foam that contains a gelatin solution of 3 to 6 weight % and has a foam density of 0.20 to 0.34 g/mL as an aspect, is gelatin foam that contains a gelatin solution of 4 weight % and has a foam density of 0.25 to 0.34 g/mL as an aspect, is gelatin foam that contains a gelatin solution of 4 weight % and has a foam density of 0.27 to 0.34 g/mL as an aspect, is gelatin foam that contains a gelatin solution of 4 weight % and has a foam density of 0.29 to 0.34 g/mL as an aspect, is gelatin foam that contains a gelatin solution of 4 weight % and has a foam density of 0.32 to 0.34 g/mL as an aspect, is gelatin foam that contains a gelatin solution of 5 weight % and has a foam density of 0.25 to 0.34 g/mL as an aspect, is gelatin foam that contains a gelatin solution of 5 weight % and has a foam density of 0.29 to 0.34 g/mL as an aspect, is gelatin foam that contains a gelatin solution of 5 weight % and has a foam density of 0.27 to 0.34 g/mL as an aspect, is gelatin foam that contains a gelatin solution of 5 weight % and has a foam density of 0.32 to 0.34 g/mL as an aspect, is gelatin foam that contains a gelatin solution of 6% and has a foam density of 0.20 to 0.34 g/mL as an aspect, and is gelatin foam that contains a gelatin solution of 6 weight % and has a foam density of 0.27 to 0.31 g/mL as an aspect, but is not limited to the range described above.

The gelatin foam having a desired foam density is dispensed to a vessel, and is frozen at −40 to −20° C., and thus, a frozen block can be obtained. The frozen block is taken out from the vessel, and preferably, is preliminarily frozen in advance at −20° C., and then, is freeze-dried by using freeze drier, and thus, a gelatin sponge can be obtained. As an aspect, drying is performed in the freeze drier at a shelf temperature of 0° C. for 48 to 240 hours under a reduced pressure of 13.3 Pa, the shelf temperature is increased to 60° C., and drying is performed for 24 to 120 hours under a reduced pressure of 0 Pa, and thus, a gelatin sponge can be obtained. Note that, a dry time may be set such that a dried gelatin sponge can be obtained, and the upper limit of the dry time can be freely changed.

In the temperature and the time at the time of performing the thermal treatment in which the cross-linkage is performed, a suitable amount according to the foam density of the gelatin solution, the type of thrombin, and the carried amount is set. For example, in the case of producing a gelatin sponge carrying approximately 50 IU/cm$^2$ of human recombinant thrombin by using a gelatin sponge produced from gelatin foam that contains a gelatin solution of 4 weight % and has a foam density of 0.29 to 0.34 g/mL, as an aspect, the thermal treatment can be performed at 120° C. for longer than or equal to 450 minutes after the thermal treatment is performed at 153° C. for longer than or equal to 200 minutes, and the thermal treatment can be further performed at 150 to 160° C. for 2 to 10 hours or at 145 to 165° C. for 2 to 20 hours. The thermal treatment can be performed at a temperature of 120 to 165° C. for 5 to 30 hours in total as an aspect, the thermal treatment can be performed at a temperature of 120 to 165° C. for 8 to 25 hours in total as an aspect, the thermal treatment can be performed at a temperature of 120 to 165° C. for 10 to 22 hours in total as an aspect, the thermal treatment can be performed at a temperature of 145 to 165° C. for 5 to 30 hours in total as an aspect, the thermal treatment can be performed at a temperature of 145 to 165° C. for 8 to 25 hours in total as an aspect, and the thermal treatment can be performed at a temperature of 145 to 165° C. for 10 to 22 hours in total as an aspect.

The cross-linked gelatin sponge can be sliced into the shape of a sheet having a desired thickness before being infiltrated in the thrombin solution. The slice may be performed before and after the cross-linking treatment. Alternatively, the cross-linked gelatin sponge may carry the thrombin, and may be freeze-dried, and then, may be sliced to have a desired thickness. The thickness when the gelatin sponge before the cross-linkage, the cross-linked gelatin sponge, or the cross-linked gelatin sponge carrying the thrombin is in the shape of a sheet can be in a range of 1.0 to 3.5 mm as an aspect, can be in a range of 1.5 to 3.3 mm as an aspect, and can be in a range of 2.0 to 3.2 mm as an aspect. Note that, the upper limit and the lower limit thereof can be arbitrarily combined, as desired.

The concentration of the gelatin solution, the foam density, and a cross-linking method are suitably combined, and thus, a hemostatic sheet carrier of a cross-linked gelatin sponge that is suitable for the hemostatic sheet of the present invention can be obtained. Herein, production examples suitable for Examples will be described, but the present invention is not necessarily limited thereto.

(2) Production of Hemostatic Sheet Carrying Thrombin

The hemostatic sheet carrier is infiltrated in the thrombin solution, and then, is freeze-dried, and thus, the hemostatic sheet of the present invention, including the gelatin sponge carrying the thrombin in the entire sponge, can be obtained. The cross-linked gelatin sponge before being sliced may be filled with the thrombin solution, and may be sliced to have a desired thickness after being freeze-dried, and thus, the hemostatic sheet of the present invention may be obtained.

A method for infiltrating the sheet carrier of the cross-linked gelatin sponge (preferably the thermally cross-linked gelatin sponge) in the thrombin solution is not particularly limited, and examples thereof include dipping, spraying, partial infiltration, the patch of a thrombin layer, and the like. Examples of the method include dipping, from the viewpoint that the entire gelatin sponge can be simply infiltrated in the thrombin.

As an aspect, the amount of thrombin solution containing a desired amount of thrombin (approximately 250 to 1500 IU/mL) that corresponding to a protein amount that is planned to be carried in the cross-linked gelatin sponge (preferably the thermally cross-linked gelatin sponge) can be dispensed to a tray. The sheet of the cross-linked gelatin sponge is applied to the tray, and is completely dipped, and then, is freeze-dried, and thus, the hemostatic sheet of the present invention, in particular, a hemostatic sheet suitable for the hemostasis during a spine surgery can be produced.

The present invention also relates to a method for performing hemostasis with respect to hemorrhage during a spine surgery of a patient.

The description of the hemostatic sheet of the present invention and the method for producing the hemostatic sheet of the present invention can be directly applied to the "gelatin sponge", the "thrombin", the "effective amount of thrombin", "hemostatic", the "sheet", "sheet-like", the "sheet carrier", the "hemostatic sheet", the "thickness", the "density", the "water absorption properties", the "shape maintaining angle in a wet condition", the "spine surgery", the "thermally cross-linked gelatin sponge", and the "foam density" of the present invention, which are used in the method.

EXAMPLES

The present invention now will be further illustrated by, but is by no means limited to, the following Examples.

<Example 1> Production 1 of Hemostatic Sheet (1-1) Production of Sheet Carrier of Thermally Cross-Linked Gelatin Sponge Gelatin (beef bones-derived gelatin, G3287P: manufactured by Nitta Gelatin Inc.) was added to purified water heated to 50° C., and was stirred and dissolved by a general-purpose stirrer (SCR-210, manufactured by Iuchi Logistics Co., Ltd.), and thus, a gelatin solution of 4% (w/w) or 6% (w/w) was prepared. The gelatin solution was put in a hopper of a continuous stirrer (TM110-GA, manufactured by AICOHSHA MFG. CO., LTD.), the gelatin solution of 4% and the gelatin solution of 6% were respectively foamed in a stirring unit at a stirring unit rotation velocity of approximately 1196 rotations/minute while performing cooling such that each product temperature was 22° C. or 21° C. and while adjusting a feeding amount of the air by supplying the gelatin solution at a constant velocity. The obtained gelatin foam having foam densities of (a) to (d) described below was dispensed to a stainless steel vessel or a polyethylene vessel, and was frozen at −40 to −30° C.:

(a) gelatin foam that contains a gelatin solution of 4 weight % and has a foam density of 0.24 g/mL;
(b) gelatin foam that contains a gelatin solution of 4 weight % and has a foam density of 0.33 g/mL;
(c) gelatin foam that contains a gelatin solution of 6 weight % has a foam density of 0.29 g/mL; and
(d) gelatin foam that contains a gelatin solution of 6 weight % and has a foam density of 0.35 g/mL.

Further, the gelatin foam was semi-thawed in an environment of 0° C., and a frozen block including the gelatin was taken out from the vessel, and then, a large frozen block was sliced with a ham slicer (LH30, manufactured by Hitachi Koki Co., Ltd.) by setting a memory of the slicer to 2.5 to 3.0 cm.

The obtained frozen block was put in a freeze drier (Lyoph-3, manufactured by ULVAC, Inc.) at −20° C. and was preliminarily frozen, was dried at a shelf temperature of 0° C. for 96 to 141 hours under a reduced pressure of 13.3 Pa, the shelf temperature was increased to 60° C., and the pressure was reduced to 0 Pa, and then, the frozen block was further dried for 24 to 72 hours, and thus, a gelatin sponge was obtained. The obtained gelatin sponge was sliced with a ham slicer (LH30, manufactured by Hitachi Koki Co., Ltd.) to be approximately 3 mm, and thus, a sliced part of the gelatin sponge was obtained. Note that, the gelatin sponge produced from the gelatin foam of (d) was cracked at the time of being sliced, and thus, the subsequent consideration was stopped.

The sliced part of the gelatin sponge obtained as described above was subjected to a thermal treatment in a dry heat sterilizer (DCH-120HL, manufactured by ALP Co., Ltd.) at 153° C. for 198 to 210 minutes, and then, was further subjected to the thermal treatment at 120° C. for 426 to 442 minutes, and thus, a sliced part of a cross-linked gelatin sponge was obtained.

The sliced part of the cross-linked gelatin sponge was not subjected to an additive thermal treatment as with (i) described below or was further subjected to the additive thermal treatment by using a dry heat sterilizer (DCH-120HL, manufactured by ALP Co., Ltd.) in any condition of (ii) to (iv) described below (hereinafter, may be referred to as an additional thermal treatment), and was cut to have a length of 50 mm and a breadth of 100 mm, and thus, hemostatic sheet carriers A to L were obtained:
(i) no additional thermal treatment;
(ii) an additional thermal treatment at 155° C. for approximately 4 hours;
(iii) an additional thermal treatment at 155° C. for approximately 8 hours; and
(iv) an additional thermal treatment at 155° C. for approximately 12 hours.

Note that, in Table 1 described below, sheets A to L indicate both of hemostatic sheets A to L carrying thrombin described below and hemostatic sheet carriers A to L, and A to L a difference between the foam densities (a) to (c) and the additional thermal treatments (i) to (iv), as described in the section of "Foam Density—Additional Thermal Treatment".

(1-2) Production of Hemostatic Sheet Carrying Thrombin

A vial of a human recombinant thrombin formulation (RECOTHROM (registered trademark) 20000 IU Topical Kit and RECOTHROM (registered trademark) 5000 IU Topical Kit, manufactured by Baxter International Inc.) was opened, dissolution was implemented again with a water for injection, and thus, a thrombin solution was obtained (284 IU/mL). The hemostatic sheet carriers A to L produced in (1-1) were dipped in a tray to which 8.8 mL of the thrombin solution was dispensed. The sheet carrier was preliminarily frozen in a freeze drier (Lyoph-3 or Lyoph-2, manufactured by ULVAC, Inc.), at −18° C. for 305 minutes, at −8° C. for 600 minutes, and at −10° C. for 125 minutes, and then, was dried at 10° C. for approximately 9 to 12 hours under a reduced pressure of 133.0 Pa and at 10° C. for 10 hours under a reduced pressure of 73.0 Pa, the temperature was increased to 25° C., and then, the sheet carrier was dried for 1.5 hours under a reduced pressure of 73.0 Pa and at 25° C. for approximately 2 to 6 hours under a reduced pressure of 0 Pa, and thus, a hemostatic sheet carrying approximately 50 IU/cm$^2$ of thrombin was produced.

(1-3) Measurement of Density of Each Hemostatic Sheet Carrier and Thickness and Density of Hemostatic Sheet Carrying Thrombin Each of the hemostatic sheet carriers obtained in (1-1) and each of the hemostatic sheets carrying the thrombin, obtained in (1-2), were cut into the shape of a square having a length and a breadth of 10 mm, the dimension was measured with a caliper, a sample weight was weighed, and the density of each of the hemostatic sheet carriers and each of the hemostatic sheets carrying the thrombin was calculated (n=20).

(1-4) Results

The density of the hemostatic sheet carrier and the density of the hemostatic sheet carrying the thrombin are shown in Table 1. In the sheets B, F, and H, the thickness of the hemostatic sheet carrying the thrombin was measured, and as a result thereof, all of the thicknesses were 2.6±0.2 mm (n=16), which were approximately homogeneous.

TABLE 1

| Sheet name | Sheet A | Sheet B | Sheet C | Sheet D |
|---|---|---|---|---|
| Foam density - additional thermal treatment | (b)-(i) | (b)-(ii) | (b)-(iii) | (b)-(iv) |
| Density (mg/cm$^3$) of hemostatic sheet carrier [Note 1] | 17.9 ± 0.9 (n = 20) | 19.3 ± 1.2 (n = 20) | 20.9 ± 0.9 (n = 20) | 20.3 ± 0.9 (n = 20) |
| Density (mg/cm$^3$) of hemostatic sheet, carrying thrombin [Note 1] | 38.1 ± 1.5 (n = 20) | 42.2 ± 2.9 (n = 20) | 43.6 ± 2.9 (n = 20) | 39.9 ± 2.4 (n = 20) |

| Sheet name | Sheet E | Sheet F | Sheet G | Sheet H |
|---|---|---|---|---|
| Foam density - additional thermal treatment | (c)-(i) | (c)-(ii) | (c)-(iii) | (c)-(iv) |
| Density (mg/cm$^3$) of hemostatic sheet carrier [Note 1] | 25.0 ± 1.3 (n = 20) | 27.5 ± 1.6 (n = 20) | 31.6 ± 2.1 (n = 20) | 28.5 ± 1.5 (n = 20) |
| Density (mg/cm$^3$) of hemostatic sheet carrying thrombin [Note 1] | 52.2 ± 1.6 (n = 20) | 51.1 ± 2.3 (n = 20) | 54.6 ± 2.3 (n = 20) | 56.0 ± 3.1 (n = 20) |

| Sheet name | Sheet I (Comparative Example) | Sheet J (Comparative Example) | Sheet K (Comparative Example) | Sheet L (Comparative Example) |
|---|---|---|---|---|
| Foam density - additional thermal treatment | (a)-(i) | (a)-(ii) | (a)-(iii) | (a)-(iv) |
| Density (mg/cm$^5$) of hemostatic sheet carrier [Note 1] | 13.9 ± 1.1 (n = 20) | 15.6 ± 0.6 (n = 20) | 16.1 ± 0.8 (n = 20) | 14.3 ± 0.3 (n = 20) |
| Density (mg/cm$^3$) of hemostatic sheet carrying thrombin [Note 1] | 34.5 ± 1.2 (n = 20) | 36.5 ± 2.1 (n = 20) | 38.6 ± 4.6 (n = 20) | 38.8 ± 2.7 (n = 20) |

Note 1:
Average value ± standard deviation

<Example 2> Production 2 of Hemostatic Sheet (2-1) Production of Sheet Carrier of Gelatin Sponge Gelatin (beef bones-derived gelatin, GGG: manufactured by Nitta Gelatin Inc.) was added to purified water heated to 40° C., and was stirred and dissolved by a general-purpose stirrer (SCR-210, manufactured by Iuchi Logistics Co., Ltd.), and thus, a gelatin solution of 4% (w/w) was prepared. The gelatin solution was put in a stirrer (manufactured by Yamana Seiko Co., Ltd.), and was stirred at a stirring unit rotation velocity of 500 rotations/minute for 2 minutes while cooling the stirrer by setting cooling water a cooling circulator (PCU-3610R, manufactured by Aspite Corporation) to 25.0° C., and then, was stirred for 22 minutes by changing the rotation velocity to 300 rotations/minute, and thus, was foamed. The obtained gelatin foam was dispensed to a stainless steel vessel, and was frozen at −40° C. in a low-temperature isothermal unit (PU-1J, manufactured by ESPEC Corp.), the temperature was increased to −2° C., and the gelatin foam was semi-thawed, and then, the stainless steel vessel was taken out from the low-temperature isothermal unit, a block including the gelatin in a semi-thawed state was taken out from the vessel, and then, was sliced to 2 to 3 mm by using a ham slicer (LH30, manufactured by Hitachi Koki Co., Ltd.), and thus, a sliced part of a gelatin sponge was obtained. The obtained sliced part was put in a freeze drier (Lyoph-2 or Lyoph-3, manufactured by ULVAC, Inc.)

preliminarily frozen at −20° C., in advance, and was dried at a shelf temperature 60° C. for approximately 10 to 17 hours under a reduced pressure of 0 Pa, and thus, the sliced part of the gelatin sponge was obtained. The obtained sliced part of the gelatin sponge was subjected to a thermal treatment at 145° C. for approximately 4 hours in a dry heat sterilizer (DCH-120HL, manufactured by ALP Co., Ltd.), and was cut to be a hemostatic sheet carrier (a length and a breadth of 40 mm).

(2-2) Production of Hemostatic Sheet Carrying Thrombin

A vial of a human recombinant thrombin formulation (RECOTHROM (registered trademark) 5000 IU Topical Kit, manufactured by Baxter International Inc.) was opened, and 720 μL of a solution (11076 IU/mL) dissolved again with a water for injection and 6.0 mg of riboflavin were suspended in cooled ethanol, and thus, 14.5 g of a thrombin solution was obtained in total. 1.7 mL of the thrombin solution was dropped on the hemostatic sheet carrier obtained in (2-1), was put in a freeze drier (Lyoph-2 and Lyoph-3, manufactured by ULVAC, Inc.), and was dried at 10° C. for approximately 21 to 22 hours under a reduced pressure of 133.3 Pa, and thus, a sheet M (Comparative Example) in Table 2 described below that is a hemostatic sheet carrying approximately 50 IU/cm$^2$ of human recombinant thrombin was produced.

(2-3) Production of Hemostatic Sheet Carrier Using Spongel (Registered Trademark)

Spongel (registered trademark) (manufactured by LTL Pharma Co., Ltd.) was subjected to a thermal treatment at 155 to 156° C. for approximately 4 hours, as with (ii) described in (1-1), and was sliced by a ham slicer (LH30, manufactured by Hitachi Koki Co., Ltd.) to have a thickness of approximately 2.6 mm, and thus, a carrier of a sheet SH in Table 2 described below was obtained. As Comparative Example, Spongel (registered trademark) was sliced to be approximately 3 mm, and thus, a carrier of a sheet Spo was obtained.

(2-4) Production of Hemostatic Sheet Carrying Thrombin Using Spongel (Registered Trademark)

The carrier of the sheet SH and the carrier of the sheet Spo, obtained in (2-3) were dipped in approximately 50 IU/cm$^2$ of the human recombinant thrombin, as with (1-2), were preliminarily frozen in a freeze drier (Lyoph-3 or Lyoph-2, manufactured by ULVAC, Inc.) at −18° C. for 305 minutes, at −8° C. for 600 minutes, and at −10° C. for 125 minutes, and then, were dried at 10° C. for approximately 5 to 14 hours under a reduced pressure of 133.0 Pa and at 10° C. for approximately 9 to 10 hours under a reduced pressure of 73.0 Pa, the temperature was increased to 25° C., and then, the carriers were semi-dried for 1.5 hours under a reduced pressure of 73.0 Pa and at 25° C. for approximately 5 to 16 hours under a reduced pressure of 0 Pa, and thus, a sheet SH and a sheet Spo (Comparative Example) in Table 2 described below that are a hemostatic sheet carrying approximately 50 IU/cm$^2$ of thrombin were produced.

(2-5) Production of Hemostatic Sheet Carrying Thrombin Using Gelfoam (Registered Trademark)

Further, as with (2-3), Gelfoam (registered trademark) (manufactured by Pfizer Inc.) sliced to be approximately 3 mm was used as a carrier, and as with (1-2), the sheet carrier dipped in approximately 50 IU/cm$^2$ of human recombinant thrombin was preliminarily frozen in in a freeze drier (Lyoph-3, manufactured by ULVAC, Inc.) at −18° C. for 305 minutes, at −8° C. for 600 minutes, and at −10° C. for 125 minutes, and then, was dried at 10° C. for approximately 14 hours under a reduced pressure of 133.0 Pa and at 10° C. for approximately 9 hours under a reduced pressure of 73.0 Pa, and the temperature was increased to 25° C., and then, the sheet carrier was semi-dried for 1.5 hours under a reduced pressure of 73.0 Pa and at 25° C. for 16 hours under a reduced pressure of 0 Pa, and thus, a sheet Gel (Comparative Example) in Table 2 described below that is a hemostatic sheet carrying approximately 50 IU/cm$^2$ of thrombin was obtained. However, Gelfoam (registered trademark) is not capable of absorbing the amount of medicinal solution necessary for carrying approximately 50 IU/cm$^2$ of thrombin, and a water absorption amount does not increase even in the case of being compressed to absorb water, and thus, it is considered that a carried amount of the thrombin is less than 50 IU/cm$^2$.

(2-6) Measurement of Thickness and Density of Each Hemostatic Sheet Carrying Thrombin and Results A sample was cut from each of the hemostatic sheets into the shape of a square having a length and a breadth of 10 mm, and the thickness was measured with a caliper. In addition, a sample weight was weighed, and the density of the hemostatic sheet was calculated. The thickness and the density of each of the sheets are shown in Table 2.

TABLE 2

| Sheet name | Sheet SH | Sheet Spo (Comparative Example) | Sheet Gel (Comparative Example) | Sheet M (Comparative Example) |
|---|---|---|---|---|
| Additional thermal treatment | 155° C. 4 hours | Absent | Absent | Absent |
| Thickness (mm) $^{Note\ 1}$ | 2.0 ± 0.3 (n = 6) | 2.4 ± 0.0 (n = 3) | 2.6 ± 0.2 (n = 4) | Unmeasured |
| Density (mg/cm$^3$) of hemostatic sheet carrying thrombin $^{Note\ 1}$ | 37.6 ± 2.1 (n = 20) | 38.9 ± 3.0 (n = 60) | Unmeasured | Unmeasured |

Note 1:
Average value ± standard deviation

<Example 3> Measurement of Shape Maintaining Angle in Wet Condition and Tensile Strength of Hemostatic Sheet Carrying Thrombin (3-1) Test of Shape Maintenance Capability in Wet Condition Each of the hemostatic sheets carrying the thrombin, produced in Example 1 and Example 2, was cut to have a length of approximately 10 mm and a breadth of approximately 20 mm, and a shape maintaining angle in a wet condition was measured. First, each of the cut hemostatic sheets was infiltrated in physiological saline for 30 minutes. Micro Spatula (manufactured by AS ONE CORPORATION) having a diameter of 2.0±0.2 mm and a length of 15 cm, as a metal rod, was placed such that both ends on the edge of a deep plastic tray vessel having a length and a breadth of 13 cm, the metal rod was horizontally retained, the sheet was placed on the metal rod such that the center line of the sheet dipped in the normal saline solution in the breadth direction was on the metal rod, and was left to stand for 5 seconds. After that, imaging was performed from the tip end side of the metal rod such that the lateral surface of the sheet in the breadth direction was a front surface until 25 seconds elapsed. Note that, in all of the tested hemostatic sheets carrying the thrombin of this test method, it was visually checked that a shape change in the sheet was completed in 5 seconds after being placed on the metal rod, and the shape change did not further occur even in the subsequent imaging (for 25 seconds), in visual observation. From the image that was imaged, the shape maintaining angle in a wet condition was measured. The test was implemented a plurality of times (n=3 to 10).

In a case where the test is imaged from the upper right, the appearance of the test, for example, is as illustrated in (vii) of FIG. 1. In this drawing, a sheet B (on the left side) and a sheet Gel (on the right side) having different shape maintaining angles in a wet condition are observed by being respectively placed and arranged on the metal rod, and it is found that shape maintenance capability in a wet condition can be determined in accordance with a difference between the shape maintaining angles in a wet condition.

(3-2) Results of Test of Shape Maintenance Capability in Wet Condition

Results are shown in Table 3.

sheet B and the sheet F, as illustrated in (v) and (vi) of FIG. 1, maintained a wide angle on the metal rod while maintaining a sheet-like shape, that is, had a large shape maintaining angle in a wet condition, and thus, had high shape maintenance capability even in a wet condition.

(3-3) Measurement of Tensile Strength

A tensile strength test of each of the hemostatic sheets carrying thrombin (a length and a breadth of approximately 15 mm), produced in Example 2, was implemented a plurality of times (n=2 to 3, when n=3, average value±standard error was calculated). The preparation was performed by using a double clip (black, extremely small, a width of 13 mm, manufactured by ASKUL Corporation) as a jig for retaining the wet hemostatic sheet, a disposable tube of 50 mL or 15 mL was attached to the opposite side, and a load amount was adjusted in accordance with the amount of water to be filled (for example, refer to (viii) of FIG. 1).

(3-4) Results of Tensile Strength

Results are as described below. Note that, the density and the shape maintaining angle in a wet condition of each of the hemostatic sheet are described in the parentheses:

the sheet SH (37.6±2.1 mg/cm$^3$, 64±5 degrees): 22±0.3 g;
the sheet B (42.2±2.9 mg/cm$^3$, 78±6 degrees): 29±0.3 g;
the sheet Spo (38.9±3.0 mg/cm$^3$, 20±3 degrees): 18±0.0 g; and
the sheet M (unmeasured, 8±2 degrees): 18 g in both of the tests implemented two times.

A tensile strength of the sheet SH had a high value, compared to the sheet M (Comparative Example) and the sheet Spo (Comparative Example). Further, the sheet B

TABLE 3

| Sheet name | Sheet A | Sheet B | Sheet C | Sheet D | Sheet E | Sheet F |
|---|---|---|---|---|---|---|
| Shape maintaining angle (degree) in wet condition [Note 1] | 56 ± 5 (n = 10) | 78 ± 6 (n = 10) | 72 ± 7 (n = 5) | 58 ± 3 (n = 5) | 104 ± 5 (n = 5) | 109 ± 6 (n = 5) |

| Sheet name | Sheet G | Sheet H | Sheet I (Comparative Example) | Sheet J (Comparative Example) | Sheet K (Comparative Example) | Sheet L (Comparative Example) |
|---|---|---|---|---|---|---|
| Shape maintaining angle (degree) in wet condition [Note 1] | 107 ± 6 (n = 5) | 121 ± 10 (n = 5) | 33 ± 4 (n = 5) | 35 ± 1 (n = 5) | 24 ± 3 (n = 5) | 23 ± 4 (n = 5) |

| Sheet name | Sheet SH | Sheet Spo (Comparative Example) | Sheet Gel (Comparative Example) | Sheet M (Comparative Example) |
|---|---|---|---|---|
| Shape maintaining angle (degree) in wet condition [Note 1] | 64 ± 5 (n = 5) | 20 ± 3 (n = 5) | 0 ± 0 (n = 3) | 8 ± 2 (n = 5) |

[Note 1] Average value ± standard deviation

The sheet Spo and the sheet Gel in which a commercially available gelatin sponge was used as a sheet carrier were softened in a wet state, and thus, as illustrated in (iii) and (iv) of FIG. 1, had a small shape maintaining angle in a wet condition. On the other hand, the sheet SH was a thermally cross-linked gelatin sponge sheet in which Spongel (registered trademark) was thermally cross-linked, and had a shape maintaining angle in a wet condition higher than that of the sheet Spo. In addition, it was checked that the hemostatic sheet of the present invention, for example, the having a high density had a higher tensile strength. From such results, it was checked that the hemostatic sheet of the gelatin sponge additionally subjected to the thermal treatment had a high tensile strength, and was less likely to be broken or ruptured during the hemostasis. In addition, the hemostatic sheet having a high shape maintaining angle in a wet condition tended to have high a tensile strength. Accordingly, it was estimated that the hemostatic sheet B was less likely to be broken or ruptured even in the case of being aspirated with an aspirator during the hemostasis.

<Example 4> Water Absorption Properties of Hemostatic Sheet Carrying Thrombin
(4-1) Evaluation Method of Water Absorption Properties The hemostatic sheet B carrying the thrombin, produced in Example 1 was cut into the shape of a square having a length and a breadth 10.0 mm to be a sample. 0.1 mL of a phosphate buffer solution (pH 7.4, manufactured by Gibco Co., Ltd.) was dropped on one surface of the sample, and a time until the liquid of the sample was not capable of being visually checked was measured (n=4). In addition, as Comparative Example, the water absorption properties were similarly evaluated with respect to a TachoSil (registered trademark) tissue sealing sheet (manufactured by CSL Limited) and Gelfoam (registered trademark) (manufactured by Pfizer Inc.). Note that, the measurement was performed with respect to both surfaces of an active surface and a non-active surface (a back surface) of the TachoSil (registered trademark) tissue sealing sheet. A maximum measurement time was 300 seconds, and in a case where the liquid was observed even after 300 seconds, a water absorption time was set to be longer than or equal to 300 seconds (a cutoff value).

(4-2) Results of Water Absorption Properties

In the sheet B, the solution was promptly absorbed immediately after being dropped, and a time required for water absorption was within 1 second.

On the other hand, in both of the TachoSil (registered trademark) tissue sealing sheet (the surface and the back surface) and Gelfoam (registered trademark), an interface tension was generated on a contact surface between the sheet and a liquid droplet, and thus, the accumulation of the liquid droplet was observed. The liquid droplet was gradually absorbed, but the liquid droplet still remained even after 300 seconds elapsed.

Accordingly, it was considered that the hemostatic sheet carrying the thrombin in which the sheet of the cross-linked gelatin sponge was a carrier had high water absorption properties, and thus, was capable of absorbing the blood instantaneously during the hemostasis. On the other hand, in Gelfoam (registered trademark) (manufactured by Pfizer Inc.) that is a formalin-modified gelatin sponge (that is, cross-linked with formaldehyde) or the TachoSil (registered trademark) tissue sealing sheet (manufactured by CSL Limited) that is a collagen sheet formulation, it was checked that it took time for water absorption.

<Example 5> Hemostasis Effect of Hemostatic Sheet Using Hemorrhage Model During Spine Surgery (5-1) Preparation of Hemorrhage Model 1 During Spine Surgery A hemorrhage model 1 of a spine surgery was prepared by using a miniature pig (NIBS, at the age of 19 to 20 months). 15 mg/kg of a ketamine hydrochloride as Introduced anesthesia was administered by the intramuscular route, and then, tracheal intubation was performed, anesthesia was maintained in a condition of mixed gas of $N_2O:O_2=2:1+1$ to 2% of isoflurane by using an inhalation anesthesia apparatus (Vigor 21 II DX, manufactured by ACOMA Medical Industry Co., Ltd.), and the breathing was managed in a condition of 10 to 15 mL/kg and 10 to 12 times/minute by using an inhalator for animal use (PRO-V mk II, manufactured by ACOMA Medical Industry Co., Ltd.). The animal was fixed in an abdominal position, was subjected to midline incision such that the muscular layer was peeled off, and a surgical field was expanded while being ensured with a retractor, and thus, the lumbus was exposed. The hemorrhage model 1 was set in which the hemorrhage during a spine surgery was imitated by the hemorrhage occurred while the lumbus was exposed.

(5-2) Hemostasis Test Method Using Hemorrhage Model 1 During Spine Surgery

The hemostatic sheet was applied to the hemorrhage of the hemorrhage model 1 of the spine surgery to press the vicinity of a hemorrhage point by using tweezers, and the hemostatic sheet was fixed with the tweezers in this state. In a case where it was possible to visually check that there was no additional hemorrhage from the hemorrhage area, from this time, a hemostasis state was continuously observed for 30 seconds without performing an additional hemostasis treatment, and it was visually checked that such a hemostasis state was maintained. In the determination of the completion of the hemostasis, in a case where the additional hemorrhage was not checked from the applied site during the observation, it was determined that the hemostasis was completed at a time point when it was possible to visually check that there was no additional hemorrhage. In addition, an elapsed time until the time point when it was determined that the hemostasis was completed from a time point when the hemostatic sheet was initially applied to the vicinity of the hemorrhage point was set to a hemostasis time.

(5-3) Hemostasis Test Using Sheet M Carrying Thrombin

The sheet M that was produced in Example 2 and was cut into the shape of a square having a length and a breadth of 20 mm was applied to the hemorrhage of the hemorrhage model 1 of the spine surgery to press the vicinity of a hemorrhage point by using tweezers while aspirating the blood due to the hemorrhage with an aspirator, and the hemostasis state was observed while fixing the sheet with the tweezers in this state. As a result of performing a test with respect to three spots of the hemorrhage point, in one spot, it was determined that the hemostasis was completed (the number of used sheets was 1, and a hemostasis time was 30 seconds), but in the other two spots, the shape of the sheet was not capable of being maintained in the case of absorbing the blood, a clump or a rupture due to the aspiration of the aspirator was observed, and the hemostasis was not capable of being performed.

In a spine surgery in the actual clinical practice, it is also necessary to perform the hemostasis with respect to the eruptive hemorrhage that is more vigorous than the hemorrhage observed in the hemorrhage model 1 of the spine surgery. For this reason, in the sheet M or the hemostatic sheet carrying the thrombin, having a shape maintaining angle in a wet condition or a tensile strength equivalent to that of the sheet M, it was estimated that the hemostasis of the eruptive hemorrhage was difficult.

(5-4) Preparation of Hemorrhage Model 2 During Spine Surgery

Figure 2:
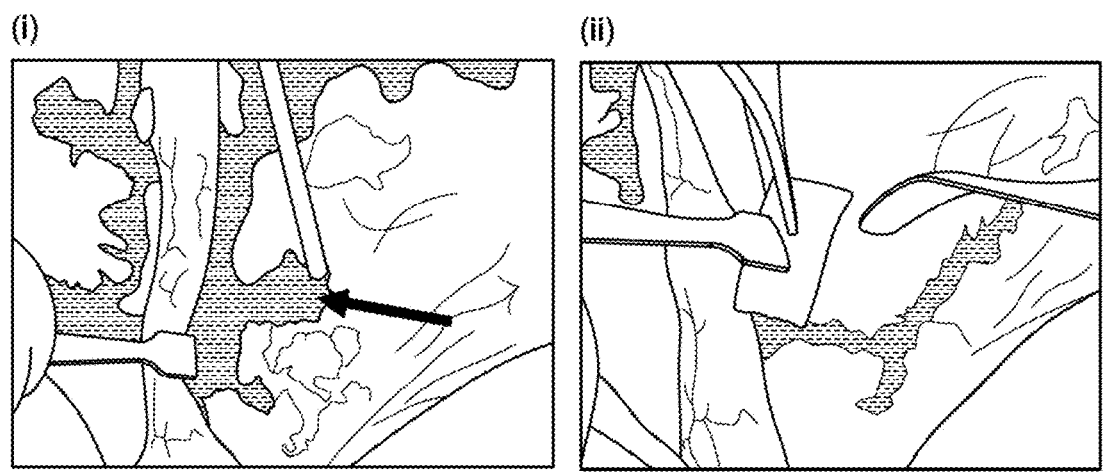
FIG. 2 is a picture illustrating a hemorrhage model 2 during a spine surgery, which is prepared in (5-5) of Example 5 and a hemostasis state in (5-7), in which (i) is a picture when eruptive hemorrhage (a spot of an arrow) reproduced, and (ii) is a picture when a sheet SH is applied to a hemorrhage spot.

In a model prepared by the method described in (5-1) by using a miniature pig (NIBS, at the age of 11 months), in which the lumbus was exposed, the vertebra was further cut by using airtome, the vertebral arch was removed such that the spinal cord was exposed, and the branched peripheral vein of the vertebral vein on the spinal cord side was sectioned such that eruptive hemorrhage occurred (refer to FIG. 2($i$)), and thus, a hemorrhage model 2 imitating vigorous eruptive hemorrhage during a spine surgery was set.

The branched peripheral vein that can be sectioned was found in a plurality of spots, and then, was immediately sectioned not to lose the sight thereof, and the eruptive hemorrhage was checked, the vicinity of the hemorrhage point was crammed with the gauze and the hemostasis was provisionally performed until a hemostasis test was started. When the hemostasis test was performed, the gauze was removed, and the reoccurrence of the eruptive hemorrhage was checked, and then, the test was started.

(5-5) Hemostasis Test Method Using Hemorrhage Model 2 During Spine Surgery

In a hemostasis test, the sheet was applied to press the vicinity of the hemorrhage point by using tweezers while aspirating the blood with an aspirator, the hemostatic sheet was fixed with the tweezers or the aspirator, and a hemorrhage situation was observed. In a case where it was determined that the hemorrhage was vigorous or the space of a hemostatic site was large, the sheet was added to press from the top, and such a manipulation was repeated until it was possible to determine that the hemorrhage was stopped from a situation or the like in which the blood was absorbed by the sheet. When the hemostatic sheet was applied, the sheet was used by being bent or rounded, in accordance with the space of the hemostatic site. In a case where it was possible to visually check that there was no additional hemorrhage from the hemorrhage area, the observation was continuously performed at least for 30 seconds without performing the additional hemostasis treatment, and it was checked that such a hemostasis state was maintained. In the determination of the completion of the hemostasis, in a case where the additional hemorrhage was not checked from the applied site during the observation, it was determined that the hemostasis was completed at a time point when it was possible to visually check that there was no additional hemorrhage. In addition, an elapsed time until the time point when it was determined that the hemostasis was completed from a time point when the hemostatic sheet was initially applied to the hemorrhage spot was set to a hemostasis time.

(5-6) Test Results Using Hemostatic Sheet of Present Invention

The sheet SH carrying the thrombin, produced in Example 2, was cut into the shape of a strip having a length of 8 mm and a breadth of 12 mm, and was applied to the hemostasis model 2. The sheet SH was applied to a hemorrhage point on five independent spots, and a hemostasis test was started (refer to FIG. 2(ii)), and as a result thereof, the shape of the sheet was maintained even after a wet state by absorbing the blood immediately after being applied, a clump or a rupture due to the aspiration of the aspirator was rarely observed, an additional hemostatic sheet was applied, and a hemostatic operation was capable of being continuously performed. In the entire hemorrhage area, it was determined that the hemostasis was completed, an average value of the hemostasis time was 2 minutes 25 seconds, and the average number of used hemostatic sheets was 4.6. In addition, it was checked that the hemostatic sheet was capable of being applied with a bare minimum size, and thus, did not occupy a surgical field.

In this test, in the sheet SH in which the completion of the hemostasis was determined, a shape maintaining angle in a wet condition was 64 degrees, and a tensile strength was 22 g. Accordingly, the hemostatic sheet of the present invention having a shape maintaining angle in a wet condition or a tensile strength higher than or equal to that of the sheet described above is expected to have an effect in the hemorrhage during a spine surgery, in particular, the hemostasis of the eruptive hemorrhage.

<Example 6> Hemostasis Effect of Hemostatic Sheet Carrying Thrombin Using Liver Damage Hemorrhage Model (6-1) Preparation of Liver Damage Hemorrhage Model A miniature pig (Goettingen minipigs, at the age of 21 months) was subjected to the laparotomy such that the liver was exposed, a plate for creating a damage including a hole having a diameter of 12 mm was pressed against the liver surface, a damage was prepared by cutting a protruding portion with a surgical knife such that hemorrhage occurred, and thus, a liver damage hemorrhage model was prepared. The animal was intravenously administered heparin sodium (500 to 3000 U, a dosed liquid amount: 0.5 to 3.0 mL) and was adjusted such that an activation clotting time was approximately 300 seconds. The activation clotting time was measured by using Actlyke MINI II (manufactured by TRITEK CO., LTD.).

(6-2) Hemostasis Test Using Liver Damage Hemorrhage Model

The hemostatic sheet carrying the thrombin, cut into the shape of a square having a length and a breadth of 20.0 mm, or a commercially available hemostatic material was placed to be in contact with a damage site, and the hemostasis was started. The sheet or the hemostatic material was fixed by being slightly pressed with a finger from the top, and thus, was applied. The finger that had pressed the sheet or the hemostatic material was removed in 1 minute after being applied, and from such a time point, the presence or absence of the hemorrhage was observed for 5 minutes. In the determination of the completion of the hemostasis, in a case where new hemorrhage was not observed on the liver surface during the observation, it was determined that the hemostasis was completed at the time point when the finger was removed, and a hemostasis time was set to 1 minute. On the other hand, in a case where the hemorrhage was observed at the time point when the finger was removed, a time until new hemorrhage was not observed on the liver surface was measured as the hemostasis time. In a case where the hemorrhage was observed in 6 minutes after the sheet or the hemostatic material was applied, the hemostasis time was set to longer than or equal to 6 minutes.

(6-3) Results of Hemostasis Test Using Sheets B, C, E, or F Carrying Thrombin or TachoSil (Registered Trademark) Tissue Sealing Sheet A hemostasis test using a liver damage hemorrhage model was performed by using the sheets B, C, E, or F carrying the thrombin, produced in Example 1, or a TachoSil (registered trademark) tissue sealing sheet. In the TachoSil (registered trademark) tissue sealing sheet, the hemorrhage was observed in three examples of five examples, even in 6 minutes after being applied. As it is described that the "active component fixing surface is patched to an adhesion or atresia site, and is compressed for 3 to 5 minutes, in general" in the appended paper of the TachoSil (registered trademark) tissue sealing sheet, in the TachoSil (registered trademark) tissue sealing sheet, a hemostasis treatment for slightly pressing the hemostatic sheet with the finger from the top was required to be performed for at least 3 minutes, and it was estimated that the hemostasis treatment for 1 minute of this test was not sufficient. On the other hand, in the sheet B carrying the thrombin, the hemorrhage was not observed in all examples (5/5), and a hemostasis time was 1 minute. In addition, in the sheet C (3/3), the sheet E (2/2), and the sheet F (2/2) carrying the thrombin, the hemorrhage was not observed.

This indicates that the hemostatic sheet of the present invention has excellent hemostasis capability with respect to the tissue surface in a general surgery, compared to the existing hemostatic sheet. In addition, the hemostatic sheet of the present invention is excellent in deformation tolerance, shape maintenance capability in a wet condition, and a tensile strength, and thus, it is estimated that the hemostatic sheet of the present invention also has excellent hemostasis capability with respect to the hemorrhage of the heart or the blood vessel in a circulatory organ surgery for allowing the hemostatic sheet to follow the concave-convex surface of the tissue.

<Example 7> Biological Absorption Properties of Hemostatic Sheet (7-1) Test Using Pepsin-Hydrochloric Acid Test Solution The hemostatic sheets A to H, and SH carrying the thrombin was cut into the shape of a square having a length and a breadth of 20 to 25 mm to have a weight of 50 mg without changing the thickness. 3100 U/mg of pepsin (manufactured by Wako Pure Chemical Industries, Ltd.) was added to in purified water, and a pepsin-hydrochloric acid test solution was prepared to be 80000±8000 U/100 mL. A conical flask of 200 mL containing the pepsin-hydrochloric acid test solution was put in a constant-temperature water bath (PERSONAL-11, manufactured by TAITEC Corporation) set at temperature of 37° C., the cut sheet was put therein, and then, was shaken (a shaking velocity of 78 times/minute), and a time when the residue of the sheet was not observed (a disappearance time) was measured (n=3). Results are shown in Table 4.

TABLE 4

| Sheet name | Sheet SH | Sheet A | Sheet B | Sheet C | Sheet D |
|---|---|---|---|---|---|
| Disappearance time (minute) | 175 | 44 | 182 | 239 | 289 |
| Sheet name | | Sheet E | Sheet F | Sheet G | Sheet H |
| Disappearance time (minute) | | 103 | 229 | 263 | 336 |

(7-2) Test Using Liver of Rat

A male rat (Wistar phylesis, at the age of 7 to 15 weeks) was subjected to anesthesia with isoflurane (2 to 3%), and was subjected to the laparotomy by sectioning the middle of abdomen such that the liver was exposed. A plate for creating a damage including a hole having a diameter of 8 mm was pressed against the liver surface, and a damage was prepared by cutting a protruding portion with a surgical knife such that hemorrhage occurred. The sheets A to H, and SH carrying the thrombin, produced in Examples 1 and 2, or a TachoSil (registered trademark) tissue sealing sheet were applied to a damage site by being cut into the shape of a square having a length and a breadth approximately of 5 mm, and were left to stand for 5 minutes. A laparotomy site was sutured by checking that the re-hemorrhage was not observed, and an analgesic drug (Meloxicam, 1 mg/kg) was subcutaneously administered. In order to prevent a decrease in the body temperature, the temperature of the animal was retained on a heat retention stand from the anesthesia to the awareness, and the animal was returned to a breeding cage after the awareness. The sheet was embedded in the body, and then, the laparotomy was performed again in the anesthesia of isoflurane (2 to 3%) with some time, and the disappearance of the sheet was checked (n=2 to 6). A moment when the disappearance of each of the sheets was checked and the number of disappearance examples in the test examples are shown in Table 5.

TABLE 5

| Sheet name | Sheet SH | Sheet A | Sheet B | Sheet C | Sheet D |
|---|---|---|---|---|---|
| Disappearance example/test example | 3/3 | 1/2 | 3/4 | 3/3 | 3/3 |
| Moment (week) for checking disappearance | 6 | 8 | 8 | 10 | 10 |

| Sheet name | Sheet E | Sheet F | Sheet G | Sheet H | TachoSil (registered trademark) |
|---|---|---|---|---|---|
| Disappearance example/test example | 0/3 | 2/3 | 1/6 | 2/6 | 0/3 |
| Moment (week) for checking disappearance | 14 | 8 | 14 | 14 | 14 |

(7-3) Discussion

In all examples (3/3), the residue of the sheet was checked at a time point of 14 weeks after embedding the TachoSil (registered trademark) tissue sealing sheet that is a hemostatic material having biological absorption properties in the body. For this reason, it is considered that the sheets SH, A to D, and F carrying the thrombin easily disappear in the biological body, compared to the TachoSil (registered trademark) tissue sealing sheet.

Note that, in the hemostatic sheet carrying the thrombin, of which the disappearance time was slow in the test using the pepsin-hydrochloric acid test solution, the disappearance moment in the test using the liver of the rat also tended to be extended. Accordingly, it is considered that even in a case where the hemostatic sheet carrying the thrombin, of which at least the disappearance time is longer than 330 minutes in the test using the pepsin-hydrochloric acid test solution, is embedded in the biological body, the disappearance moment is extended.

<Example 8> Check of Deformation Tolerance of Hemostatic Sheet Carrying Thrombin (8-1) Measurement The presence or absence of a crack or a rupture in the case of deforming the hemostatic sheet carrying the thrombin was tested. The sheets B, H, and J carrying the thrombin of Example 1 were cut to have a length of 10 mm and a breadth of 20 mm. Each of the cut sheets was pushed and bent such that the breadth of the sheet is wound around a cylindrical curved surface that is a lateral surface of a tube (BioClean Tip 1000 µL, manufactured by Mettler-Toledo Rainin, LLC) having a diameter of approximately 7 mm, and the presence or absence of a crack or a rupture of the sheet was checked.

(8-2) Results

In all examples (5/5), a crack or a rupture was not observed in the sheets B and J, but in all examples (5/5), a crack was observed in the sheet H. It was observed that the deformation tolerance decreased as the density increased. Accordingly, it is estimated that the hemostatic sheet of the present invention, having deformation tolerance higher than or equal to that of the sheets B and J, has properties of not causing a crack even in the case of being deformed in order to closely attach the hemostatic sheet in a dry state to the hemorrhage area, and thus, the hemostatic material can be applied to the hemorrhage area having a limited space in which the hemostatic material can be used such as during a spine surgery.

<Example 9> Check of Expansion of Hemostatic Sheet Carrying Thrombin (9-1) Measurement The hemostatic sheet produced by using the same method as that of the sheet B carrying the thrombin of Example 1 was cut into the shape of a square in a range of 10±0.5 mg, and thus, four samples (a length and a breadth of 15.01±0.39 mm, and a thickness: 3.11±0.08 mm) were obtained. The sample was dipped in a petri dish containing purified water, the lateral surface of the sample was imaged (a magnification of 10 times) by using a microscope (VW-9000, manufactured by Keyence Corporation) after a constant period of time elapsed, and thus, an image was obtained. The width and the thickness of the hemostatic sheet were measured on the image. A measurement point was set to be before a wet state, immediately after a wet state, in 1 hour, in 3 hours, and in 6 hours, and a change rate with respect to a dry state was calculated as a swelling rate (n=4).

(9-2) Results

Results are shown in Table 6. An expansion rate in a horizontal direction was approximately 6% in a wet condition, and no further expansion was observed. On the other hand, in an expansion rate in the thickness direction, a temporal reduction was observed. In terms of the volume of the hemostatic sheet carrying the thrombin, there was volume expansion of approximately 10 to 11% in 1 hour after a wet state, but the volume in 3 hours after a wet state was identical to the volume before a wet state. Accordingly, the hemostatic sheet of the present invention that is equivalent to the sheet is suitable during a spine surgery.

TABLE 6

| Time after wet state | Immediately after wet state | 1 hour | 3 hours | 6 hours |
| --- | --- | --- | --- | --- |
| Expansion rate (%) in horizontal direction | 5.9 ± 5.4 | 5.9 ± 6.1 | 3.9 ± 5.5 | 2.8 ± 3.6 |
| Expansion rate (%) in thickness direction | −2.4 ± 8.0 | −0.8 ± 8.1 | −6.6 ± 2.3 | −9.2 ± 6.3 | n = 4, Average value ± standard deviation

INDUSTRIAL APPLICABILITY

The hemostatic sheet carrying the thrombin according to the present invention is useful to hemostasis during a surgery, in particular, hemostasis during a spine surgery.

The invention claimed is:

1. A hemostatic sheet comprising a gelatin sponge carrying 10 to 200 IU/cm$^2$ of thrombin,
   wherein A) the hemostatic sheet has a density of 30 to 55 mg/cm$^3$ and a thickness in a range of 1.0 to 3.5 mm, and
   B) when the sheet cut to have a length of 10.0±1.0 mm and a breadth of 20.0±1.0 mm is dipped in physiological saline for 30 minutes, and then, is placed on a horizontally retained cylindrical metal rod having a diameter of 2.0±0.2 mm and a length of greater than or equal to 11.0 mm such that a center line of the sheet in the breadth direction is coincident with the rod, and is left to stand for 5 to 30 seconds, a shape maintaining angle in a wet condition, represented by a spread angle between both ends of the sheet (innermost ends) centered on the metal rod, is 55 to 120 degrees.

2. The hemostatic sheet according to claim 1, wherein the hemostatic sheet has water absorption properties of absorbing 0.1 mL of a phosphate buffer solution dropped on the sheet cut to have a length and a breadth of 10.0±1.0 mm within 10 seconds.

3. The hemostatic sheet according to claim 1, wherein when cut to have a weight of 50.0±2.5 mg, is put in a conical flask containing a 80000±8000 U/100 mL pepsin-hydrochloric acid test solution, and the conical flask is shaken at a velocity at which an aqueous surface of the pepsin-hydrochloric acid test solution shakes, in a constant-temperature water bath set at 37±1° C., a disappearance time when a residue of the hemostatic sheet is not visually observed is shorter than 330 minutes.

4. The hemostatic sheet according to claim 3, wherein the disappearance time is shorter than 300 minutes.

5. The hemostatic sheet according to claim 1, wherein the thrombin comprises human recombinant thrombin.

6. The hemostatic sheet according to claim 1, wherein the gelatin sponge carries 50±15 IU/cm$^2$ of thrombin, and the thrombin comprises human recombinant thrombin.

7. The hemostatic sheet according to claim 1, wherein the shape maintaining angle in a wet condition according to claim 1, is 64 to 100 degrees.

8. The hemostatic sheet according to claim 1, wherein the density is 35 to 55 mg/cm$^3$.

9. The hemostatic sheet according to claim 1, wherein the density is 37 to 52 mg/cm$^3$.

10. The hemostatic sheet according to claim 1, wherein the hemostatic sheet configured for hemostasis during a spine surgery.

11. The hemostatic sheet according to claim 1, wherein the hemostatic sheet substantially contains no cross-linking agent.

12. The hemostatic sheet according to claim 1, wherein the gelatin sponge is a thermally cross-linked gelatin sponge.

13. The hemostatic sheet according to claim 12, wherein the thermally cross-linked gelatin sponge is produced by performing a thermal treatment with respect to a gelatin sponge obtained by foaming and drying 3 to 6 weight % of a gelatin solution to have a foam density of 0.20 to 0.34 g/mL, at a temperature of 120 to 165° C. for 10 to 30 hours in total.

14. The hemostatic sheet according to claim 1, comprising the gelatin sponge carrying an effective amount of thrombin, wherein the hemostatic sheet is produced by a production method including:
  (1) a step of producing a thermally cross-linked gelatin sponge by performing a thermal treatment with respect to a gelatin sponge obtained by foaming and drying 3 to 6 weight % of a gelatin solution to have a foam density of 0.20 to 0.34 g/mL, at a temperature of 120 to 165° C. for 10 to 30 hours in total; and
  (2) a step of producing a cross-linked gelatin sponge carrying an effective amount of thrombin by infiltrating the thermally cross-linked gelatin sponge obtained in the step (1) in a thrombin solution, and then, by drying the gelatin sponge, and
  the dried gelatin sponge or the thermally cross-linked gelatin sponge obtained in the step (1), or the cross-linked gelatin sponge carrying an effective amount of thrombin, obtained in the step (2), is sliced to have a thickness of 1.0 to 3.5 mm.

15. A method for performing hemostasis with respect to hemorrhage of a patient during a spine surgery, by using the hemostatic sheet according to claim 1.

16. A hemostatic sheet comprising a gelatin sponge carrying 10 to 200 IU/cm$^2$ of human recombinant thrombin, configured for hemostasis during a spine surgery,
  wherein A) the hemostatic sheet has a thickness in a range of 1.0 to 3.5 mm,
  B) the hemostatic sheet has a density of 30 to 55 mg/cm$^3$,
  C) the hemostatic sheet has water absorption properties of absorbing 0.1 mL of a phosphate buffer solution dropped on the sheet cut to have a length and a breadth of 10.0±1.0 mm within 10 seconds, and
  D) when the sheet cut to have a length of 10.0±1.0 mm and a breadth of 20.0±1.0 mm is dipped in physiological saline for 30 minutes, and then, is placed on a horizontally retained cylindrical metal rod having a diameter of 2.0±0.2 mm and a length of greater than or equal to 11.0 mm such that a center line of the sheet in the breadth direction is coincident with the rod, and is left to stand for 5 to 30 seconds, a shape maintaining angle in a wet condition, represented by a spread angle between both ends of the sheet (innermost ends) centered on the metal rod, is 55 to 120 degrees.

17. A hemostatic sheet comprising a gelatin sponge carrying 50±15 IU/cm$^2$ of human recombinant thrombin, configured for hemostasis during a spine surgery,
  wherein A) the hemostatic sheet has a thickness in a range of 1.0 to 3.5 mm,
  B) the hemostatic sheet has a density of 30 to 55 mg/cm$^3$,
  C) the hemostatic sheet has water absorption properties of absorbing 0.1 mL of a phosphate buffer solution dropped on the sheet cut to have a length and a breadth of 10.0±1.0 mm within 10 seconds, and
  D) when the sheet cut to have a length of 10.0±1.0 mm and a breadth of 20.0±1.0 mm is dipped in physiological saline for 30 minutes, and then, is placed on a horizontally retained cylindrical metal rod having a diameter of 2.0±0.2 mm and a length of greater than or equal to 11.0 mm such that a center line of the sheet in the breadth direction is coincident with the rod, and is left to stand for 5 to 30 seconds, a shape maintaining angle in a wet condition, represented by a spread angle between both ends of the sheet (innermost ends) centered on the metal rod, is 55 to 120 degrees.

18. A hemostatic sheet comprising a gelatin sponge carrying 50±15 IU/cm$^2$ of human recombinant thrombin and substantially containing no cross-linking agent, configured for hemostasis during a spine surgery,
  wherein A) the hemostatic sheet has a thickness in a range of 1.0 to 3.5 mm,
  B) the hemostatic sheet has a density of 30 to 55 mg/cm$^3$,
  C) the hemostatic sheet has water absorption properties of absorbing 0.1 mL of a phosphate buffer solution dropped on the sheet cut to have a length and a breadth of 10.0±1.0 mm within 10 seconds, and
  D) when the sheet cut to have a length of 10.0±1.0 mm and a breadth of 20.0±1.0 mm is dipped in physiological saline for 30 minutes, and then, is placed on a horizontally retained cylindrical metal rod having a diameter of 2.0±0.2 mm and a length of greater than or equal to 11.0 mm such that a center line of the sheet in the breadth direction is coincident with the rod, and is left to stand for 5 to 30 seconds, a shape maintaining angle in a wet condition, represented by a spread angle between both ends of the sheet (innermost ends) centered on the metal rod, is 55 to 120 degrees.

19. A method for producing a hemostatic sheet including a gelatin sponge carrying an effective amount of thrombin, the method comprising:
  (1) a step of producing a thermally cross-linked gelatin sponge by performing a thermal treatment with respect to a gelatin sponge obtained by foaming and drying 3 to 6 weight % of a gelatin solution to have a foam density of 0.20 to 0.34 g/mL, at a temperature of 120 to 165° C. for 10 to 30 hours in total; and
  (2) a step of producing a cross-linked gelatin sponge carrying an effective amount of thrombin by infiltrating the thermally cross-linked gelatin sponge obtained in the step (1) in a thrombin solution, and then, by drying the gelatin sponge, wherein the dried gelatin sponge or the thermally cross-linked gelatin sponge obtained in the step (1), or the cross-linked gelatin sponge carrying an effective amount of thrombin, obtained in the step (2), is sliced to have a thickness of 1.0 to 3.5 mm.

\* \* \* \* \*